(12) United States Patent
Kisiel et al.

(10) Patent No.: US 12,188,093 B2
(45) Date of Patent: *Jan. 7, 2025

(54) DETECTING CHOLANGIOCARCINOMA

(71) Applicant: Mayo Foundation for Medical Education and Research, Rochester, MN (US)

(72) Inventors: John B. Kisiel, Rochester, MN (US); David A. Ahlquist, Rochester, MN (US); William R. Taylor, Lake City, MN (US); Douglas W. Mahoney, Elgin, MN (US); Tracy C. Yab, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 239 days.

This patent is subject to a terminal disclaimer.

(21) Appl. No.: 17/120,518

(22) Filed: Dec. 14, 2020

(65) Prior Publication Data

US 2021/0102264 A1 Apr. 8, 2021

Related U.S. Application Data

(63) Continuation of application No. 16/242,695, filed on Jan. 8, 2019, now Pat. No. 10,900,090, which is a continuation of application No. 14/864,158, filed on Sep. 24, 2015, now Pat. No. 10,184,154.

(60) Provisional application No. 62/055,737, filed on Sep. 26, 2014.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,486,530 A | 12/1984 | David et al. |
| 4,683,195 A | 7/1987 | Mullis et al. |
| 4,683,202 A | 7/1987 | Mullis |
| 4,735,214 A | 4/1988 | Berman |
| 4,859,610 A | 8/1989 | Maggio |
| 4,965,188 A | 10/1990 | Mullis et al. |
| 5,011,769 A | 4/1991 | Duck et al. |
| 5,124,246 A | 6/1992 | Urdea et al. |
| 5,137,806 A | 8/1992 | Lemaistre et al. |
| 5,196,167 A | 3/1993 | Guadagno et al. |
| 5,198,365 A | 3/1993 | Grow et al. |
| 5,288,609 A | 2/1994 | Engelhardt et al. |
| 5,338,671 A | 8/1994 | Scalice et al. |
| 5,352,775 A | 10/1994 | Albertsen |
| 5,362,623 A | 11/1994 | Vogelstein |
| 5,403,711 A | 4/1995 | Walder et al. |
| 5,409,818 A | 4/1995 | Davey et al. |
| 5,475,610 A | 12/1995 | Atwood et al. |
| 5,494,810 A | 2/1996 | Barany et al. |
| 5,508,169 A | 4/1996 | Deugau et al. |
| 5,527,676 A | 6/1996 | Vogelstein |
| 5,538,871 A | 7/1996 | Nuovo et al. |
| 5,541,308 A | 7/1996 | Hogan |
| 5,602,756 A | 2/1997 | Atwood et al. |
| 5,612,473 A | 3/1997 | Wu et al. |
| 5,624,802 A | 4/1997 | Urdea et al. |
| 5,639,611 A | 6/1997 | Wallace et al. |
| 5,648,212 A | 7/1997 | Albertsen |
| 5,660,988 A | 8/1997 | Duck et al. |
| 5,670,325 A | 9/1997 | Lapidus et al. |
| 5,691,454 A | 11/1997 | Albertsen |
| 5,710,264 A | 1/1998 | Urdea et al. |
| 5,741,650 A | 4/1998 | Lapidus et al. |
| 5,773,258 A | 6/1998 | Birch et al. |
| 5,783,666 A | 7/1998 | Albertsen |
| 5,786,146 A | 7/1998 | Herman |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,891,651 A | 4/1999 | Roche |
| 5,914,230 A | 6/1999 | Liu et al. |
| 5,928,870 A | 7/1999 | Lapidus et al. |
| 5,952,178 A | 9/1999 | Lapidus et al. |
| 5,955,263 A | 9/1999 | Vogelstein |

(Continued)

FOREIGN PATENT DOCUMENTS

| | | |
|---|---|---|
| CA | 2902916 | 8/2018 |
| CN | 102021233 | 4/2011 |

(Continued)

OTHER PUBLICATIONS

Kim et al. Arch Pathol Lab Med 131:923-930. (Year: 2007).*
Shire et al. BMP3 is hypermethylated and may function as a tumor suppressor in cholangiocarcinoma. Cancer Res 68 (9_Supplement):4282. (Year: 2008).*
Sriraksa et al. Aberrant DNA Methylation at Genes Associated with a Stem Cell-like Phenotype in Cholangiocarcinoma Tumors. Cancer Prev Res (Phila) 6(12):1348-1355. (Year: 2013).*
Sriraksa Supplementary Table 3 ([online] Dec. 2013 [retrieved on Sep. 9, 2023] retrieved from https://aacrjournals.org/cancerpreventionresearch/article/6/12/1348/50090/Aberrant-DNA-Methylation-at-Genes-Associated-with#supplementary-data (Year: 2013).*

(Continued)

*Primary Examiner* — Samuel C Woolwine
(74) *Attorney, Agent, or Firm* — Casimir Jones, S.C.; Peter J. Schlueter

(57) ABSTRACT

Provided herein is technology relating to detecting neoplasia and particularly, but not exclusively, to methods, compositions, and related uses for detecting neoplasms such as cholangiocarcinoma.

2 Claims, 3 Drawing Sheets

Specification includes a Sequence Listing.

(56) References Cited

U.S. PATENT DOCUMENTS

| | | |
|---|---|---|
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,020,137 A | 2/2000 | Lapidus et al. |
| RE36,713 E | 5/2000 | Vogelstein |
| 6,063,573 A | 5/2000 | Kayyem |
| 6,090,543 A | 7/2000 | Prudent et al. |
| 6,090,566 A | 7/2000 | Vogelstein |
| 6,110,677 A | 8/2000 | Western et al. |
| 6,110,684 A | 8/2000 | Kemper et al. |
| 6,114,124 A | 9/2000 | Albertsen |
| 6,121,001 A | 9/2000 | Western et al. |
| 6,143,529 A | 11/2000 | Lapidus et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,470 B1 | 5/2001 | Sidransky |
| 6,235,502 B1 | 5/2001 | Weissman et al. |
| 6,245,515 B1 | 6/2001 | Vogelstein |
| 6,248,229 B1 | 6/2001 | Meade |
| 6,251,594 B1 | 6/2001 | Gonzalgo et al. |
| 6,265,171 B1 | 7/2001 | Herman et al. |
| 6,329,178 B1 | 12/2001 | Patel et al. |
| 6,335,167 B1 | 1/2002 | Pinkel et al. |
| 6,395,524 B2 | 5/2002 | Loeb et al. |
| 6,406,857 B1 | 6/2002 | Shuber et al. |
| 6,413,727 B1 | 7/2002 | Albertsen |
| 6,541,217 B2 | 4/2003 | Hiraoka et al. |
| 6,602,695 B2 | 8/2003 | Patel et al. |
| 6,605,451 B1 | 8/2003 | Marmaro et al. |
| 6,630,314 B2 | 10/2003 | Nair et al. |
| 6,677,312 B1 | 1/2004 | Vogelstein |
| 6,800,617 B1 | 10/2004 | Vogelstein |
| 6,872,816 B1 | 3/2005 | Hall et al. |
| RE38,916 E | 12/2005 | Vogelstein |
| 7,037,650 B2 | 5/2006 | Gonzalgo et al. |
| 7,087,414 B2 | 8/2006 | Gerdes et al. |
| 7,087,583 B2 | 8/2006 | Vogelstein |
| 7,122,364 B1 | 10/2006 | Lyamichev et al. |
| 7,195,878 B2 | 3/2007 | Cleator |
| 7,267,955 B2 | 9/2007 | Vogelstein |
| 7,368,233 B2 | 5/2008 | Shuber et al. |
| 7,432,050 B2 | 10/2008 | Markowitz |
| 7,485,402 B2 | 2/2009 | Arai |
| 7,485,418 B2 | 2/2009 | Goggins |
| 7,485,420 B2 | 2/2009 | Markowitz |
| 7,514,219 B2 | 4/2009 | Showe et al. |
| 7,662,594 B2 | 2/2010 | Kong et al. |
| 7,695,913 B2 | 4/2010 | Cowens et al. |
| 7,794,929 B2 | 9/2010 | Baylin et al. |
| 7,960,112 B2 | 6/2011 | Budiman et al. |
| 8,067,178 B2 | 11/2011 | Baker et al. |
| 8,114,587 B2 | 2/2012 | Gite et al. |
| 8,198,024 B2 | 6/2012 | Cowens et al. |
| 8,304,214 B2 | 11/2012 | Gerdes et al. |
| 8,343,738 B2 | 1/2013 | Millar et al. |
| 8,361,720 B2 | 1/2013 | Oldham-Haltom et al. |
| RE44,596 E | 11/2013 | Stroun et al. |
| 8,673,555 B2 | 3/2014 | Taylor et al. |
| 8,715,937 B2 | 5/2014 | Zou et al. |
| 8,741,567 B2 | 6/2014 | He et al. |
| 8,808,990 B2 | 8/2014 | Lidgard et al. |
| 8,916,344 B2 | 12/2014 | Zou et al. |
| 8,969,046 B2 | 3/2015 | Van Engeland et al. |
| 8,980,107 B2 | 3/2015 | Domanico et al. |
| 8,993,341 B2 | 3/2015 | Bruinsma et al. |
| 8,999,176 B2 | 4/2015 | Domanico et al. |
| 9,000,146 B2 | 4/2015 | Bruinsma et al. |
| 9,096,893 B2 | 8/2015 | Allawi et al. |
| 9,115,386 B2 | 8/2015 | Rao et al. |
| 9,163,278 B2 | 10/2015 | Bruinsma et al. |
| 9,169,511 B2 | 10/2015 | Lidgard et al. |
| 9,212,392 B2 | 12/2015 | Allawi et al. |
| 9,315,853 B2 | 4/2016 | Domanico et al. |
| 9,422,592 B2 | 8/2016 | Morris et al. |
| 9,428,746 B2 | 8/2016 | Holmberg et al. |
| 9,506,116 B2 | 11/2016 | Ahlquist et al. |
| 9,518,990 B2 | 12/2016 | Wild et al. |
| 9,546,403 B1 | 1/2017 | Warren et al. |
| 9,637,792 B2 | 5/2017 | Ahlquist et al. |
| 9,657,511 B2 | 5/2017 | Lidgard et al. |
| 9,726,670 B2 | 8/2017 | Ataman-Onal et al. |
| 9,891,223 B2 | 2/2018 | Beaulieu et al. |
| 9,896,730 B2 | 2/2018 | Kan et al. |
| 9,982,310 B2 | 5/2018 | Ahlquist et al. |
| 9,994,911 B2 | 6/2018 | Ahlquist et al. |
| 10,011,878 B2 | 7/2018 | Ahlquist et al. |
| 10,030,272 B2 | 7/2018 | Ahlquist et al. |
| 10,167,513 B2 | 1/2019 | Ahuja et al. |
| 10,184,154 B2 | 1/2019 | Kisiel et al. |
| 10,292,687 B2 | 5/2019 | Maguire et al. |
| 10,301,680 B2 | 5/2019 | Ahlquist et al. |
| 10,327,742 B2 | 6/2019 | Fitzgerald et al. |
| 10,370,726 B2 | 8/2019 | Ahlquist et al. |
| 10,385,406 B2 | 8/2019 | Allawi et al. |
| 10,435,755 B2 | 10/2019 | Ahlquist et al. |
| 10,465,248 B2 | 11/2019 | Allawi et al. |
| 10,519,510 B2 | 12/2019 | Ahlquist et al. |
| 10,648,025 B2 | 5/2020 | Allawi et al. |
| 10,648,035 B2 | 5/2020 | Agarwal et al. |
| 10,704,081 B2 | 7/2020 | Lidgard et al. |
| 10,822,638 B2 | 11/2020 | Allawi et al. |
| 10,883,144 B2 | 1/2021 | Ahlquist et al. |
| 10,900,090 B2 | 1/2021 | Kisiel et al. |
| 11,078,539 B2 | 8/2021 | Ahlquist et al. |
| 11,118,228 B2 | 9/2021 | Allawi et al. |
| 11,345,949 B2 | 5/2022 | Allawi et al. |
| 11,365,451 B2 | 6/2022 | Ahlquist et al. |
| 11,634,781 B2 | 4/2023 | Louwagie |
| 2003/0143606 A1 | 7/2003 | Olek et al. |
| 2003/0224040 A1 | 12/2003 | Baylin et al. |
| 2004/0175733 A1 | 9/2004 | Andersen et al. |
| 2004/0234960 A1 | 11/2004 | Hogan |
| 2005/0021240 A1 | 1/2005 | Berlin et al. |
| 2005/0048527 A1 | 3/2005 | Allawi et al. |
| 2005/0214926 A1 | 9/2005 | Zielenski et al. |
| 2005/0239101 A1 | 10/2005 | Sukumar et al. |
| 2006/0134663 A1 | 6/2006 | Harkin et al. |
| 2006/0147955 A1 | 7/2006 | Allawi et al. |
| 2006/0171952 A1 | 8/2006 | Mather et al. |
| 2006/0216714 A1 | 9/2006 | Kanaoka |
| 2006/0253259 A1 | 11/2006 | Fernandez |
| 2007/0048748 A1 | 3/2007 | Williams et al. |
| 2007/0054295 A1 | 3/2007 | Spivack |
| 2007/0161062 A1 | 7/2007 | Tacke et al. |
| 2007/0172823 A1 | 7/2007 | Steinberg et al. |
| 2007/0202513 A1 | 8/2007 | Shuber et al. |
| 2007/0202525 A1 | 8/2007 | Quake et al. |
| 2008/0003571 A1 | 1/2008 | McKernan et al. |
| 2008/0039413 A1 | 2/2008 | Morris et al. |
| 2008/0081333 A1 | 4/2008 | Mori et al. |
| 2008/0213870 A1 | 9/2008 | Cao et al. |
| 2008/0025447 A1 | 10/2008 | Foekens et al. |
| 2009/0077685 A1 | 3/2009 | Buehler et al. |
| 2009/0203011 A1 | 8/2009 | Liebenberg et al. |
| 2009/0208505 A1 | 8/2009 | Samuels |
| 2009/0239212 A1 | 9/2009 | Beever et al. |
| 2009/0253142 A1 | 10/2009 | Allawi et al. |
| 2009/0286237 A1 | 11/2009 | Fitzgerald et al. |
| 2010/0075334 A1 | 3/2010 | Kim et al. |
| 2010/0092953 A1 | 4/2010 | Dietrich et al. |
| 2010/0167940 A1 | 7/2010 | Feinberg |
| 2010/0317000 A1 | 12/2010 | Zhu |
| 2011/0009277 A1 | 1/2011 | Devos et al. |
| 2011/0045999 A1 | 2/2011 | Willman et al. |
| 2011/0123990 A1 | 5/2011 | Baker et al. |
| 2011/0136687 A1 | 6/2011 | Olek et al. |
| 2011/0160446 A1 | 6/2011 | Ritt et al. |
| 2011/0183328 A1 | 7/2011 | Taylor et al. |
| 2011/0256538 A1 | 10/2011 | Su et al. |

(56) References Cited

U.S. PATENT DOCUMENTS

| | | |
|---|---|---|
| 2011/0287424 A1 | 11/2011 | Chen |
| 2011/0287968 A1 | 11/2011 | Weinhausel et al. |
| 2011/0318738 A1 | 12/2011 | Jones et al. |
| 2012/0009597 A1 | 1/2012 | Lao-Sirieix et al. |
| 2012/0028835 A1 | 2/2012 | Wild et al. |
| 2012/0034605 A1 | 2/2012 | Hinoda et al. |
| 2012/0053073 A1 | 3/2012 | Kassis et al. |
| 2012/0122088 A1 | 5/2012 | Zou |
| 2012/0122106 A1 | 5/2012 | Zou |
| 2012/0164110 A1 | 6/2012 | Feinberg et al. |
| 2012/0164238 A1 | 6/2012 | Louwagie |
| 2012/0246748 A1 | 9/2012 | Guo et al. |
| 2012/0288867 A1 | 11/2012 | Lidgard et al. |
| 2012/0288868 A1 | 11/2012 | Bruinsma et al. |
| 2013/0012410 A1 | 1/2013 | Zou et al. |
| 2013/0022974 A1 | 1/2013 | Chinnaiyan |
| 2013/0065228 A1 | 3/2013 | Hinoue et al. |
| 2013/0244235 A1 | 9/2013 | Ahlquist et al. |
| 2013/0288241 A1 | 10/2013 | Ahuja et al. |
| 2013/0288247 A1 | 10/2013 | Mori et al. |
| 2013/0296738 A1 | 11/2013 | Swain et al. |
| 2014/0017233 A1 | 1/2014 | Bais et al. |
| 2014/0057262 A1 | 2/2014 | Ahlquist et al. |
| 2014/0087382 A1 | 3/2014 | Allawi et al. |
| 2014/0137274 A1 | 5/2014 | Ishikawa |
| 2014/0162894 A1 | 6/2014 | Hatchwell et al. |
| 2014/0193813 A1 | 7/2014 | Bruinsma et al. |
| 2014/0194607 A1 | 7/2014 | Bruinsma et al. |
| 2014/0194608 A1 | 7/2014 | Bruinsma et al. |
| 2014/0221242 A1 | 8/2014 | Sukumar et al. |
| 2014/0274748 A1 | 9/2014 | Ahlquist et al. |
| 2014/0342946 A1 | 11/2014 | Kuriakose et al. |
| 2014/0358448 A1 | 12/2014 | Tai et al. |
| 2015/0126374 A1 | 5/2015 | Califano |
| 2015/0240318 A1 | 8/2015 | Van Engeland et al. |
| 2015/0259750 A1 | 9/2015 | Andavolu et al. |
| 2015/0275314 A1 | 10/2015 | Ahlquist et al. |
| 2015/0292029 A1 | 10/2015 | Agarwal et al. |
| 2016/0010081 A1 | 1/2016 | Allawi et al. |
| 2016/0010163 A1 | 1/2016 | Preston et al. |
| 2016/0078167 A1 | 3/2016 | Rosner et al. |
| 2016/0081671 A1 | 3/2016 | Lubinski et al. |
| 2016/0090634 A1 | 3/2016 | Kisiel et al. |
| 2016/0168643 A1 | 6/2016 | Ahlquist et al. |
| 2016/0194721 A1 | 7/2016 | Allawi et al. |
| 2016/0194723 A1 | 7/2016 | Louwagie |
| 2016/0251727 A1 | 9/2016 | Ahlquist et al. |
| 2016/0281175 A1 | 9/2016 | Weinhausel et al. |
| 2016/0312299 A1 | 10/2016 | Tyler et al. |
| 2016/0333424 A1 | 11/2016 | Morris et al. |
| 2017/0058356 A1 | 3/2017 | Allawi et al. |
| 2017/0073772 A1 | 3/2017 | Ahlquist et al. |
| 2017/0121704 A1 | 5/2017 | Allawi et al. |
| 2017/0121757 A1 | 5/2017 | Lidgard et al. |
| 2017/0253924 A1 | 9/2017 | Lu et al. |
| 2017/0321286 A1 | 11/2017 | Allawi et al. |
| 2017/0335401 A1 | 11/2017 | Allawi et al. |
| 2018/0037958 A1 | 2/2018 | Ahlquist et al. |
| 2018/0066320 A1 | 3/2018 | Taylor et al. |
| 2018/0087113 A1 | 3/2018 | Knudsen et al. |
| 2018/0143198 A1 | 5/2018 | Wen et al. |
| 2018/0245157 A1 | 8/2018 | Allawi et al. |
| 2019/0085406 A1 | 3/2019 | Mortimer et al. |
| 2019/0127808 A1 | 5/2019 | Kisiel et al. |
| 2019/0161804 A1 | 5/2019 | Ahlquist et al. |
| 2019/0177769 A1 | 6/2019 | Allawi et al. |
| 2019/0218601 A1 | 7/2019 | Allawi et al. |
| 2019/0249263 A1 | 8/2019 | Ahlquist et al. |
| 2019/0330702 A1 | 10/2019 | Allawi et al. |
| 2020/0071767 A1 | 3/2020 | Sepulveda et al. |
| 2020/0131588 A1 | 4/2020 | Ahlquist et al. |
| 2020/0172982 A1 | 6/2020 | Ahlquist et al. |
| 2020/0248233 A1 | 8/2020 | Allawi et al. |
| 2020/0291458 A1 | 9/2020 | Lidgard et al. |
| 2020/0370114 A1 | 11/2020 | Song et al. |
| 2021/0102263 A1 | 4/2021 | Ahlquist et al. |
| 2021/0348239 A1 | 11/2021 | Ahlquist et al. |
| 2021/0381066 A1 | 12/2021 | Ahlquist et al. |
| 2022/0071605 A1 | 3/2022 | Eisele et al. |
| 2022/0349009 A1 | 11/2022 | Taylor et al. |
| 2023/0046033 A1 | 2/2023 | Zubin et al. |

FOREIGN PATENT DOCUMENTS

| | | |
|---|---|---|
| CN | 102292458 | 12/2011 |
| CN | 104762301 | 7/2015 |
| CN | 104781421 | 7/2015 |
| DE | 102010043541 | 1/2012 |
| EP | 1366715 | 12/2003 |
| EP | 2391729 | 12/2011 |
| EP | 2497834 | 9/2012 |
| EP | 2698436 | 2/2014 |
| EP | 2201131 | 11/2014 |
| EP | 2435830 | 12/2014 |
| EP | 3301446 | 4/2018 |
| JP | 2008-502890 | 1/2008 |
| JP | 2009-095262 | 5/2009 |
| JP | 2010-533853 | 10/2010 |
| JP | 2015-006163 | 1/2015 |
| KR | 10-2016-0128136 | 11/2016 |
| WO | WO 1992/02258 | 2/1992 |
| WO | WO 1993/10820 | 6/1993 |
| WO | WO 1994/22892 | 10/1994 |
| WO | WO 1994/24144 | 10/1994 |
| WO | WO 1995/000669 | 1/1995 |
| WO | WO 1995/015373 | 6/1995 |
| WO | WO 1997/025925 | 7/1997 |
| WO | WO 1997/046705 | 12/1997 |
| WO | WO 1999/028498 | 6/1998 |
| WO | 00/26401 | 5/2000 |
| WO | WO 2001/042781 | 6/2001 |
| WO | WO 2001/094634 | 12/2001 |
| WO | WO 2002/070755 | 9/2002 |
| WO | WO 2003/087390 | 10/2003 |
| WO | WO 2005/014154 | 2/2005 |
| WO | WO 2005/023091 | 3/2005 |
| WO | WO 2005/038041 | 4/2005 |
| WO | WO 2005/038051 | 4/2005 |
| WO | WO 2005/098050 | 10/2005 |
| WO | WO 2005/113769 | 12/2005 |
| WO | WO 2005/124356 | 12/2005 |
| WO | WO 2006/084132 | 8/2006 |
| WO | WO 2006/094149 | 9/2006 |
| WO | WO 2006/113770 | 10/2006 |
| WO | 2007/116417 | 10/2007 |
| WO | WO 2007/121489 | 10/2007 |
| WO | WO 2007/134779 | 11/2007 |
| WO | WO 2008/073303 | 6/2008 |
| WO | WO 2008/084219 | 7/2008 |
| WO | WO 2008/100913 | 8/2008 |
| WO | WO 2009/035447 | 3/2009 |
| WO | WO 2009/102788 | 8/2009 |
| WO | WO 2009/114836 | 9/2009 |
| WO | WO 2012/067831 | 5/2010 |
| WO | WO 2010/074924 | 7/2010 |
| WO | 2010/086389 | 8/2010 |
| WO | WO 2010/089538 | 8/2010 |
| WO | WO 2011/058316 | 5/2011 |
| WO | WO 2011/084108 | 7/2011 |
| WO | 2011/119934 | 9/2011 |
| WO | 2011/126768 | 10/2011 |
| WO | WO 2011/133935 | 10/2011 |
| WO | WO 2012/034170 | 3/2012 |
| WO | 2012/088298 | 6/2012 |
| WO | WO 2012/037128 | 8/2012 |
| WO | WO 2012/106525 | 8/2012 |
| WO | 2012/155072 | 11/2012 |
| WO | 2012/175562 | 12/2012 |
| WO | WO 2013/026104 | 2/2013 |
| WO | WO 2013/058868 | 4/2013 |
| WO | WO 2013/033627 | 5/2013 |
| WO | WO 2013/070950 | 5/2013 |
| WO | WO 2013/103889 | 7/2013 |
| WO | WO 2013/116375 | 8/2013 |

(56) References Cited

FOREIGN PATENT DOCUMENTS

| | | |
|---|---|---|
| WO | WO 2013/142545 | 9/2013 |
| WO | WO 2013/171504 | 11/2013 |
| WO | WO 2014/026768 | 2/2014 |
| WO | WO 2014/039556 | 3/2014 |
| WO | WO 2014/089241 | 6/2014 |
| WO | WO 2014/159650 | 10/2014 |
| WO | WO 2014/159652 | 10/2014 |
| WO | WO 2014/160117 | 10/2014 |
| WO | WO 2015/066695 | 5/2015 |
| WO | WO 2015/095689 | 6/2015 |
| WO | WO 2015/116837 | 8/2015 |
| WO | WO 2015/153283 | 10/2015 |
| WO | WO 2015/153284 | 10/2015 |
| WO | 2016/097120 | 6/2016 |
| WO | WO 2016/094813 | 6/2016 |
| WO | WO 2016/094839 | 6/2016 |
| WO | WO 2016/160454 | 10/2016 |
| WO | WO 2017/040627 | 3/2017 |
| WO | WO 2017/075061 | 5/2017 |
| WO | WO 2017/129716 | 8/2017 |
| WO | WO 2017/176630 | 10/2017 |
| WO | WO 2017/180886 | 10/2017 |
| WO | WO 2017/191274 | 11/2017 |
| WO | WO 2017/192221 | 11/2017 |
| WO | WO 2017/210372 | 12/2017 |
| WO | WO 2017/223216 | 12/2017 |
| WO | WO 2018/017740 | 1/2018 |
| WO | WO 2018/045322 | 3/2018 |
| WO | WO 2018/140781 | 8/2018 |
| WO | WO 2018/160576 | 9/2018 |
| WO | WO 2019/010429 | 1/2019 |
| WO | WO 2019/035100 | 2/2019 |
| WO | WO 2019/108626 | 6/2019 |
| WO | WO 2020/089691 | 5/2020 |
| WO | WO 2020/112869 | 6/2020 |
| WO | WO 2020/118274 | 6/2020 |
| WO | WO 2020/154665 | 7/2020 |
| WO | WO 2020/206256 | 10/2020 |
| WO | WO 2020/236939 | 11/2020 |
| WO | WO 2020/264220 | 12/2020 |
| WO | WO 2021/041726 | 3/2021 |
| WO | WO 2021/055508 | 3/2021 |
| WO | WO 2021/076969 | 4/2021 |
| WO | WO 2021/087275 | 5/2021 |
| WO | WO 2021/212031 | 10/2021 |
| WO | WO 2021/226071 | 11/2021 |
| WO | WO 2021/226074 | 11/2021 |
| WO | WO 2022/039904 | 2/2022 |
| WO | WO 2022/040306 | 2/2022 |
| WO | WO 2022/165247 | 8/2022 |
| WO | WO 2022/187227 | 9/2022 |
| WO | WO 2022/187695 | 9/2022 |
| WO | WO 2023/081796 | 5/2023 |

OTHER PUBLICATIONS

GeneCards® record for ZNF781 [online] [retrieved on Sep. 9, 2023] retrieved from https://www.genecards.org/cgi-bin/carddisp.pl?gene=ZNF781 (Year: 2023).*

Ahlquist D et al. (2010) "Next Generation Stool DNA Testing for Detection of Colorectal Neoplasia—Early Marker Evaluation", presented at Colorectal Cancer: Biology to Therapy, American Association for Cancer Research.

Ahlquist D.A. et al., "Novel use of hypermethylated DNA markers in stool for detection of colorectal cancer: a feasibility study." Gastroenterology, 2002;122(Suppl):A40.

Ahlquist D.A., et al., "Colorectal cancer screening by detection of altered human DNA in stool: feasibility of a multitarget assay panel." Gastroenterology, 2000, 119(5):1219-27.

Ahlquist et al., "Next-generation stool DNA test accurately detects colorectal cancer and large adenomas." Gastroenterology (2012), 142, pp. 248-256.

Asai et al. "IKZF1 deletion is associated with a poor outcome in pediatric B-cell precursor acute lymphoblastic leukemia in Japan." Cancer Med. 2013; 2:412-9.

Aust DE, "Mutations of the BRAF gene in ulcerative colitis-related colorectal carcinoma." Int. J. Cancer (2005), 115, pp. 673-677.

Azuara et al. "Novel Methylation Panel for the Early Detection of Colorectal Tumors in Stool DNA." Clinical Colorectal Cancer, vol. 9, No. 3, pp. 168-176, Jul. 2010.

Belinsky S.A., et al., "Promoter Hypermethylation of Multiple Genes in Sputum Precedes Lung Cancer Incidence in a High-Risk Cohort." Cancer Res, 2006;66:3338-44.

Bell et al., "c-Ki-ras gene mutations in dysplasia and carcinomas complicating ulcerative colitis." Br J Cancer (1991), 64, pp. 174-178.

Biankin et al (2003) "Molecular pathogenesis of precursor lesions of pancreatic ductal adenocarcinoma" Pathology 35:14-24.

Brune, et al. (2008). "Genetic and epigenetic alterations of familial pancreatic cancers." Cancer Epidemiol Biomarkers Prev. 17 (12): 3536-3542.

Cairns et al., "Guidelines for colorectal cancer screening and surveillance in moderate and high risk groups." Gut (2010); 59, pp. 666-689.

Cameron et al (1995) "Adenocarcinoma of the esophagogastric junction and Barrett's esophagus" Gastroenterology 109: 1541-1546.

Camoes et al. "Potential downstream target genes of aberrant ETS transcription factors are differentially affected in Ewing's sarcoma and prostate carcinoma." PLoS ONE. 2012;7:e49819.

Campbell et al. "Aberrant expression of the neuronal transcription factor FOXP2 in neoplastic plasma cells." British journal of haematology. 2010; 149:221-30.

Chen W.D., et al., "Detection in Fecal DNA of Colon Cancer-Specific Methylation of the Nonexpressed Vimentin Gene." J Natl Cancer Inst 2005;97:1124-32.

Eads, et al. (1999). "CpG island hypermethylation in human colorectal tumors is not associated with DNA methyltransferase overexpression." Cancer Res. 59: 2302-2306.

Ebert M.P., et al., "Aristaless-like homeobox-4 gene methylation is a potential marker for colorectal adenocarcinomas." Gastroenterology 2006;131:1418-30.

Edge, S.; Fritz, A.G.; Greene, F.L.; Trotti, A. (Eds.), AJCC Cancer Staging Manual. 7th ed: Springer, New York; 2010; Book—only table of contents provided.

Garrity-Park et al. "Methylation status of genes in non-neoplastic mucosa from patients with ulcerative colitis-associated colorectal cancer." Am J Gastroenterol (2010), 105, pp. 1610-1619.

Glockner, et al. (2009). "Methylation of TFPI2 in stool DNA: a potential novel biomarker for the detection of colorectal cancer." Cancer Res. 69: 4691-4699.

Goggins, M. "Molecular markers of early pancreatic cancer." J Clin Oncol 2005; 23: 4524.

Gonzalgo, et al. (1997) "Identification and characterization of differentially methylated regions of genomic DNA by methylation-sensitive arbitrarily primed PCR." Cancer Res. 57: 594-599.

Gonzalgo, et al. (1997). "Rapid quantitation of methylation differences at specific sites using methylation-sensitive single nucleotide primer extension (Ms-SNuPE)." Nucleic Acids Res. 25 (12): 2529-2531.

Grady W.M., et al., "Detection of Aberrantly Methylated hMLH1 Promoter DNA in the Serum of Patients with Microsatellite Unstable Colon Cancer 1." Cancer Res, 2001;61:900-2.

Grutzmann et al., "Sensitive Detection of Colorectal Cancer in Peripheral Blood by Septin 9 DNA Methylation Assay." PLoS ONE (2008), 3:e3759.

Gu et al. "Genome-scale DNA methylation mapping of clinical samples at single-nucleotide resolution." Nat Methods. 2010; 7:133-6.

Gu, et al. (2011). "Preparation of reduced representation bisulfite sequencing libraries for genome-scale DNA methylation profiling." Nature Protocols. 6 (4): 468-481.

Gurung et al. "Menin epigenetically represses Hedgehog signaling in MEN1 tumor syndrome." Cancer research. 2013;73:2650-8.

Herman, et al. (1996). "Methylation-specific PCR: A novel PCR assay for methylation status of CpG islands." Proc. Natl. Acad. Sci. USA. 93: 9821-9826.

(56) References Cited

OTHER PUBLICATIONS

Hibi et al. (2010) "Methylation of the TFPI2 gene is frequently detected in advanced gastric carcinoma" Anticancer Res 30: 4131-3.
Hibi, et al. (2010). "Methylation of TFPI2 gene is frequently detected in advanced well-differentiated colorectal cancer." Anticancer Res. 30: 1205-1207.
Hirota et al., "pS2 expression as a possible diagnostic marker of colorectal carcinoma in ulcerative colitis." Oncol Rep (2000), 7, pp. 233-239.
Holzmann et al., "Comparative analysis of histology, DNA content, p53 and Ki-ras mutations in colectomy specimens with long-standing ulcerative colitis." Int J Cancer (1998) 76, pp. 1-6.
Hong, et al. (2008). "Multiple genes are hypermethylated in intraductal papillary mucinous neoplasms of the pancreas." Mod Pathol. 21 912): 1499-1507.
Hoque M.O., et al., "Quantitative methylation-specific polymerase chain reaction gene patterns in urine sediment distinguish prostate cancer patients from control subjects." J Clin Oncol, 2005;23:6569-75.
Howe, et al., "Annual report to the nation on the status of cancer, 1975-2003, featuring cancer among U.S. Hispanic/Latino populations." Cancer (2006) 107, pp. 1711-1742.
Imperiale et al., "Fecal DNA versus fecal occult blood for colorectal-cancer screening in an average-risk population." N Engl J Med (2004), 351, pp. 2704-2714.
International Search Report and Written Opinion, Int'l Patent Application No. PCT/US2015/022749, mailed Aug. 19, 2015, 12 pages.
International Search Report and Written Opinion, Int'l Patent Application No. PCT/US2015/022751, mailed Aug. 26, 2015, 25 pages.
International Search Report mailed Jun. 10, 2013 from related International Patent Application No. PCT/US2013/027227.
Issa et al., "Accelerated Age-related CpG Island Methylation in Ulcerative Colitis." Cancer Res (2001), 61, pp. 3573-3577.
Itzkowitz S.H., et al., "Improved fecal DNA test for colorectal cancer screening." Clin Gastroenterol Hepatol 2007;5:111-7.
Itzkowitz et al. "Diagnosis and management of dysplasia in patients with inflammatory bowel diseases." Gastroenterology (2004) 126, pp. 1634-1648.
Jacobs et al. "Dysregulated methylation at imprinted genes in prostate tumor tissue detected by methylation microarray." BMC Urol. 2013;13:37.
Jess et al., "Risk of intestinal cancer in inflammatory bowel disease: a population-based study from olmsted county, Minnesota." Gastroenterology (2006) 130, pp. 1039-1046.
Jiao et al. "Somatic mutations in the Notch, NF-KB, PIK3CA, and Hedgehog pathways in human breast cancers." Genes, chromosomes & cancer. 2012; 51:480-9.
Kaiser. (2008). "Cancer genetics. A detailed genetic portrait of the deadliest human cancers." Science. 321: 1280-1281.
Kann L., et al., "Improved marker combination for detection of de novo genetic variation and aberrant DNA in colorectal neoplasia." Clin Chem 2006;52:2299-302.
Kawai, et al. (1994). "Comparison of DNA methylation patterns among mouse cell lines by restriction landmark genomic screening." Mol. Cell Biol. 14 (11): 7421-7427.
Ruppenthal et al. "TWIST1 Promoter Methylation in Primary Colorectal Carcinoma" Pathol. Oncol. Res., 2011, 17:867-872.
Baxter, Eva "Investigating the association between BRAFv600E and methylation in sporadic colon cancer" PhD The University of Edinburgh, 2011.
Chen "Expression and promoter methylation analysis of ATP-binding cassette genes in pancreatic cancer" Oncology Reports, 2012, 27:265-269.
Kisiel, et al. "Su1340 Detection of Colorectal Cancer and Polyps in Patients with Inflammatory Bowel Disease by Novel Methylated Stool DNA Markers" Gastroenerology, vol. 146, No. 5, May 1, 2014, pp. S-440.

Taylor et al. "109 Discovery of Novel DNA Methylation Markers for the Detection of Colorectal Neopolasia: Selection by Methylome-Wide Analysis" Gastroenterology, vol. 146, No. 5, May 1, 2014, pp. S-30.
Haag S, et al., "Regression of Barrett's esophagus: the role of acid suppression, surgery, and ablative methods." Gastrointest Endosc. Aug. 1999;50(2):229-40.
Qiu et al. Hypermethylation of ACP1, BMP4, and TSPYL5 in Hepatocellular Carcinoma and Their Potential Clinical Significance, Digestive Diseases and Sciences, Sep. 19, 2015, vol. 61, No. 1, pp. 149-157.
International Search Report and Written Opinion, International Patent Application No. PCT/US2017/049915, mailed Jan. 18, 2018.
Gao et al. "Global Analysis of DNA Methylation in hepatocellular cariconma by a liquid hybridization cpature-based bisulfite sequencing approach" Clinical Epigenetics, vol. 7, No. 86, Aug. 2015.
Barat et al. "Comparative Correlation Structure of Colon Cancer Locus Specific Methylation: Characterisation of Patient Profiles and Potential Markers across 3 Array-Based Datasets" J. of Cancer, vol. 6, pp. 795-811, Jul. 2015.
Sloane et al. "Epigenetic inactivation of the candidate tumor suppressor USP44 is a frequent and early event in colorectal neoplasia" Epigenetics, vol. 9, No. 8, pp. 1092-1100, Aug. 2014.
Kisiel Aga Abstracts #469, S-84, May 2013.
Tan et al. "Variable promoter region CpG island methylation of the putative tumor suppressor gene Connexin 26 in breast cancer" Carcinogenesis. 2002 23(2): 231-236.
Jin et al. "A multicenter, Double-blinded Validation study of methylation biomarkers for progression prediction in Barrett's Esophagus" Cancer Research, May 15, 2009, vol. 69, pp. 4112-4115.
Kaz et al. "DNA methylation profiling in Barrett's esophagus and esophageal adenocarcinoma reveals unique methylation signatures and molecular subclasses" Epigenetics, Dec. 1, 2011, vol. 6, pp. 1403-1412.
Zhai et al. "Genome-wide DNA Methylation Profiling of Cell-Free Serum DNA in Esophageal Adenocarcinoma and Barrett Esophagus" Neoplasia, Jan. 11, 2012, vol. 14, No. 1, pp. 29-33.
International Search Report, International Application No. PCT/US2016/023782, mailed Sep. 1, 2016.
Abbaszadegan, "Stool-based DNA testing, a new noninvasive method for colorectal cancer screening, the first report from Iran," World Journal of gastroenterology: WJG, vol. 13, p. 1528-1533, 2007.
Ahlquist et al., 1984, "HemoQuant, a new quantitative assay for fecal hemoglobin. Comparison with Hemoccult." Ann Intern Med, 101: 297-302.
Ahlquist et al., 1985, "Fecal blood levels in health and disease. A study using HemoQuant." N Engl J Med, 312: 1422-8.
Ahlquist et al., 1989, "Patterns of occult bleeding in asymptomatic colorectal cancer." Cancer, 63: 1826-30.
Ahlquist et al., 1993, "Accuracy of fecal occult blood screening for colorectal neoplasia. A prospective study using Hemoccult and HemoQuant tests." JAMA, 269: 1262-7.
Ahlquist et al., 2000, "Colorectal cancer screening by detection of altered human DNA in stool: feasibility of a multitarget assay panel." Gastroenterology, 119: 1219-27.
Ahlquist et al., 2008, "Stool DNA and occult blood testing for screen detection of colorectal neoplasia." Ann Intern Med, 149: 441-501.
Allison et al., 2007, "Screening for colorectal neoplasms with new fecal occult blood tests: update on performance characteristics." J Natl Cancer Inst, 99: 1462-70.
Anderson et al. Am. J. of Gastroenterology, Abstracts S1033, Oct. 2015.
Cameron et al. Blood, vol. 94, No. 7, pp. 2445-2451, Oct. 1999.
De Kok, 2003, "Quantification and integrity analysis of DNA in the stool of colorectal cancer patients may represent a complex alternative to fecal occult blood testing." Clin Chem, 49: 2112-3.
Esteller et al. "Inactivation of Glutathione S-Transferase P1 Gene by Promoter Hypermethylation in Human Neoplasia" Cancer Resarch, vol. 58, pp. 4515-4518, Oct. 1998.
Feng "Conservation and divergence of methylation patterning in plants and animals" PNAS 2010 vol. 107, No. 19, pp. 8689-8694.

(56) References Cited

OTHER PUBLICATIONS

Grutzmann, et al. (2008), "Sensitive detection of colorectal cancer in peripheral blood by septin—DNA methylation assay," PLoS ONE 3(11): e3759 which is 8 pages long.

Guzinska-Ustymowicz et al., (2009), "Correlation between proliferation makers: PCNA, Ki-67, MCM-2 and antiapoptopic protein Bcl2 in colorectal cancer," Anticancer Research. 29:3049-3052.

Hardcastle et al., 1996, "Randomised controlled trial of faecal-occult-blood screening for colorectal cancer." Lancet, 348: 1472-7.

Harewood et al., 2000, "Fecal occult blood testing for iron deficiency: a reappraisal." Dig Dis, 18(2): 75-82.

Harewood et al., 2002, "Detection of occult upper gastrointestinal tract bleeding: performance differences in fecal occult blood tests." Mayo Clin Proc, 77: 23-28.

Heresbach et al., 2006, "Review in depth and meta-analysis of controlled trials on colorectal cancer screening by faecal occult blood test." Eur J Gastroenterol Hepatol, 18: 427-33.

Hoang et al., 1997, "BAT-26, an indicator of the replication error phenotype in colorectal cancers and cell lines." Cancer Res, 57: 300-3.

Imperiale et al. "Multitarget Stool DNA Testing for Colorectal-Cancer Screening" New England Journal of Medicine, vol. 370, No. 14, Apr. 3, 2014, pp. 1287-1297.

Imperiale et al., 2004, "Fecal DNA versus fecal occult blood for colorectal-cancer screening in an average-risk population." N Engl J Med, 351: 2704-14.

International Search Report and Written Opinion mailed Dec. 28, 2011 from International Patent Application No. PCT/US2011/029959, international filing date Mar. 25, 2011.

Jemal et al., 2007, "Cancer statistics, 2007." CA Cancer J Clin, 57: 43-66.

Kariya et al., 1987, "Revision of consensus sequence of human Alu repeats—a review." Gene, 53: 1-10.

Kim, H., et al., "Noninvasive molecular biomarkers for the detection of colorectal cancer," BMB Reports, 2008, vol. 41, No. 10, pp. 685-692.

Kronborg et al., 1996, "Randomised study of screening for colorectal cancer with faecal-occult-blood test." Lancet, 348: 1467-71.

Kronborg et al., 2004, "Randomized study of biennial screening with a faecal occult blood test: results after nine screening rounds." Scand J Gastroenterol, 39: 846-51.

Levin et al., 2008, "Screening and surveillance for the early detection of colorectal cancer and adenomatous polyps, 2008: a joint guideline from the American Cancer Society, the US Multi-Society Task Force on Colorectal Cancer, and the American College of Radiology." CA Cancer J Clin, 58: 130-60.

Lokk et al. "Methylation Markers of Early-Stage Non-Small Cell Lung Cancer" PLOS ONE, vol. 7, No. 6, e398013, Jun. 2012.

Mandel et al., 1993, "Reducing mortality from colorectal cancer by screening for fecal occult blood. Minnesota Colon Cancer Control Study." N Engl J Med, 328: 1365-71.

Meissner, 2006, "Patterns of colorectal cancer screening uptake among men and women in the United States." Cancer Epidemiol Biomarkers Prev, 15: 389-94.

Melle, et al. (2005), "Discovery and identification of a-defensins as low abundant, tumor-derived serum markers in colorectal cancer," 129(1): 66-73 abstract only.

Melotte, et al., (Jul. 1, 2009): "N-myc downstream-regulated gene 4 (NDRG4): a candidate tumor suppressor gene and potential biomarker for colorectal cancer," J. Natl Cancer Inst 101: 916-927.

Meuwis, "Contribution of proteomics to colorectal cancer diagnosis," Acta Endoscopica, vol. 37, p. 295-303, including translation, 2007.

Muller et al., 2004, "Methylation changes in faecal DNA: a marker for colorectal cancer screening?" Lancet, 363: 1283-5.

Nosho, et al. (2008): "PIK3CA mutation in colorectal cancer: Relationship with genetic and epigenetic alterations," Neoplasia. 10(6) 034-541, abstract only.

Olson et al., 2005, "DNA stabilization is critical for maximizing performance of fecal DNA-based colorectal cancer tests." Diagn Mol Pathol, 14: 183-91.

Osborn et al., 2005, "Stool screening for colorectal cancer: molecular approaches." Gastroenterology, 128: 192-206.

Pao et al. "The endothelin receptor B (EDNRB) promoter displays heterogeneous, site specific methylation patterns in normal and tumor cells" Human Molecular Genetics, vol. 10, No. 9, pp. 903-910.

Park, et al. (2002), "Expressiono f melanoma antigen-encoding genes (MAGE) by common primers for MAGE-A1 to -A6 in colorectal carcinomas among Koreans," J. Korean Med. Sci 17: 497-501.

Saitoh et al. (1995), "Intestinal protein loss and bleeding assessed by fecal hemoglobin, transferrin, albumin, and alpha-1-antitrypsin levels in patients with colorectal diseases," Digestion. 56(1): 67-75, abstract only.

Sambrook et al., 1989, Fritsch, E.F., Maniatis, T. (ed.), Molecular Cloning, Cold Spring Harbor Lab. Press, Cold Spring Harbor, N.Y., 30 pages.

Samowitz et al., 1999, "BAT-26 and BAT-40 instability in colorectal adenomas and carcinomas and germline polymorphisms." Am J Path, 154: 1637-41.

Schwartz et al., 1983, "The "HemoQuant" test: a specific and quantitative determination of heme (hemoglobin) in feces and other materials." Clin Chem, 29: 2061-7.

Schwartz et al., 1985, "Quantitative fecal recovery of ingested hemoglobin-heme in blood: comparisons by HemoQuant assay with ingested meat and fish." Gastroenterology, 89: 19-26.

Singh et al., 2006, "Risk of developing colorectal cancer following a negative colonoscopy examination: evidence for a 10-year interval between colonoscopies." JAMA, 295: 2366-73.

Summons to attend oral proceedings, European patent application No. 11760295.3, mailed Mar. 4, 2016.

Tibble, et al. (2001), "Faecal capprotectin and faecal occult blood tests in the diagnosis of colorectal carcinoma and adenoma.," Gut. 49:402-408.

Uchida, et al. (1994), "Immunochemical detection of human lactoferrin in feces as a new marker for inflammatorygastrointestinal disorders and colon cancer," Clinical Biochemistry. 27(4)L 259-264, abstract only.

Wang, "Gene expression profiles and molecular markers to predict recurrence of duke's B Colon Cancer," vol. 22, pp. 1564-1571, 2004.

Wen, et al. (2006), "Frequence epigenetic silencing of the bome morphogenic protein 2 gene through methylation in gastic carcinomas," Onogene. 25:2666-2673.

Winawer et al., 1993, "Screening for colorectal cancer with fecal occult blood testing and sigmoidoscopy." J Natl Cancer Inst, 85: 1311-8.

Wittekind et al. (1986), "Localization of CEA, HCG, lysozyme, alpha-1-antitrypsin, and alpha-1-antichymotrypsin in gastric cancer and prognosis," Virchows Arch 409:715-724.

Young, "Fecal Immunochemical Tests (FIT) vs. Office-based guaiac fecal occult blood test (FOBT)," Practical Gastroenterology, Colorectal Cancer, series 3, p. 46-56, 2004.

Zijlstra et al., 2002, "A quantitative analysis of rate-limiting steps in the metastatic cascade using human-specific real-time polymerase chain reaction." Cancer Res, 62: 7083-92.

Zou et al., 2006, "A sensitive method to quantify human long DNA in stool: relevance to colorectal cancer screening." Cancer Epidemiol Biomarkers Prev, 15: 1115-9.

Zou, et al. (2007), "Highly methylated genes in colorectal neoplasia: Implications for screening," Cancer Epidemilogy Biomarkers Prev. 16(12): 2686-2696.

Zou, et al., "High Detection Rates of Colorectal Neoplasia by Stool DNA Testing with a Novel Digital Melt Curve Assay," Gastroenterology, vol. 136, No. 2, Feb. 1, 2009, pp. 459-470.

Zou, et al., "T2034 Stool DNA and Occult Blood for Detection of Colorectal Cancer: Complementary Markers," Gastroenterology, vol. 136, No. 5, May 1, 2009, p. A-625.

Supplemental Search Report, EP Patent Application No. 15772326.3, mailed Oct. 6, 2017.

(56) References Cited

OTHER PUBLICATIONS

Buck et al. "Design Strategies and Performance of Custom DNA Sequencing Primers" Biotechniques, 1999, 27(3): 528-536.
Naumov "Genome-scale analysis of DNA methylation in colorectal cancer using Infinium HumanMethylation450 BeadChips" Epigenetics, 2013, vol. 8, issue 9, pp. 921-934.
Kisiel et al. "New DNA Methylation Markers for Pancreatic Cancer: Discovery, Tissue Validation, and Pilot Testing in Pancreatic Juice" Clinical Cancer Research, vol. 21, No. 19, May 28, 2015, pp. 4473-4481.
Sen-Yo et al. "TWIST1 hypermethylation is observed in pancreatic cancer" Biomedical Reports; 1:33-33, 2013.
Kisiel et al. (AGA Abstracts, VS-68, vol. 138, No. 5, May 2010).
Kisiel et al. "Stool DNA testing for the detection of pancreatic cancer: assessment of methylation marker candidates." Cancer. 2012; 118:2623-31.
Kisiel, et al. (2011). "Stool DNA screening for colorectal cancer: opportunities to improve value with next generation tests." J Clin Gastroenterol. 45 (4): 301-8.
Kober et al. "Methyl-CpG binding column based identification of nine genes hypermethylated in colorectal cancer." Molecular carcinogenesis. 2011; 50:846-56.
Kraus, et al., "Inflammation and colorectal cancer," Current Opinion in Pharmacology, vol. 9, No. 4, pp. 405-410 (2009).
Kuppuswamy et al. "Single nucleotide primer extension to detect genetic diseases: Experimental application to hemophilia B (factor IX) and cystic fibrosis genes" (1991) Proc. Natl. Acad. Sci. USA 88: 1143-1147.
LAIRD. (2010). "Principles and challenges of genome-wide DNA methylation analysis." Nat Rev Genet. 11: 191-203.
Lashner BA, Am J Gastroenterol (1999), 94, pp. 456-462.
Lee et al. "Pituitary homeobox 2 (PITX2) protects renal cancer cell lines against doxorubicin toxicity by transcriptional activation of the multidrug transporter ABCB1." International journal of cancer Journal international du cancer. 2013; 133:556-67.
Leung W.K., et al., "Detection of epigenetic changes in fecal DNA as a molecular screening test for colorectal cancer: A feasibility study" Clin Chem 2004; 50(11):2179-82.
Levin B, Gastroenterology (2008); 134, pp. 1570-1595.
Li et al. "Association between Galphai2 and ELMO1/Dock180 connects chemokine signalling with Rac activation and metastasis." Nat Commun. 2013; 4:1706.
Lim, et al. (2010). "Cervical dysplasia: assessing methylation status (Methylight) of CCNA1, DAPK1, HS3ST2, PAX1 and TFPI2 (to improve diagnostic accuracy." Gynecol Oncol. 119: 225-231.
Lin, et al., Identification of disease-associated DNA methylation in intestinal tissues from patients with inflammatory bowel disease, Clinical Genetics, vol. 80, No. 1, pp. 59-67 (2011).
Liu et al. "Medulloblastoma expresses CD1d and can be targeted for immunotherapy with NKT cells." Clin Immunol. 2013;149:55-64.
Ma, et al. (2011). "MicroRNA-616 induces androgen-independent growth of prostate cancer cells by suppressing expression of tissue factor pathway inhibitor TFPI-2." Cancer Res. 71: 583-592.
Maeda, et al., "DNA hypermethylation in colorectal neoplasms and inflammatory bowel disease: a mini review," Inflammapharmacology, vol. 14, No. 5-6, pp. 204-206 (2006).
Matsubayashi, et al. (2006). "DNA methylation alterations in the pancreatic juice of patients with suspected pancreatic disease." Cancer Res. 66: 1208-1217.
Meissner, et al. (2008). "Genome-scale DNA methylation maps of pluripotent and differentiated cells." Nature. 454: 766-70.
Melotte et al., (JNCL, vol. 101, No. 13, pp. 916-927, Jul. 2009).
Muller H.M., et al., "Methylation changes in faecal DNA: a marker for colorectal cancer screening?" The Lancet 2004;363:1283-5.
Obusez et al. (Inflammatory Bowel Diseases: vol. 14, Issue pS42, Dec. 2008, P-0106).
Obusez et al. (Int. J. Colorectal Dis. Vol. 26, pp. 951-953, 2011).
Odze Rd, Am J Surg Pathol (2000), 24, pp. 1209-1216.
Olaru, et al., "Unique patterns of CpG island methylation in inflammatory bowel disease-associated colorectal cancers," Inflammatory Bowel Diseases, vol. 18, No. 4, pp. 641-648 (Epub Aug. 9, 2011).
Olson, J et al. "DNA Stabilization Is Critical for Maximizing Performance of Fecal DNA-Based Colorectal Cancer Tests" Diagn Mol Pathol (2005) 14, pp. 183-191.
Omura, et al. (2008). "Genome-wide profiling of methylated promoters in pancreatic adenocarcinoma." Cancer Biol Ther. 7 (7): 1146-1156.
Omura, et al. (2009). "Epigenetics and epigenetic alterations in pancreatic cancer." Int. J. Clin Exp Pathol. 2: 310-326.
Osborn NK, and Ahlquist DA, "Stool screening for colorectal cancer: molecular approaches." Gastroenterology 2005;128:192-206.
Osborn, et al., "Aberrant methylation of the eyes absent 4 gene in ulcerative colitis-associated dysplasia," Clinical Gastroenterology and Hepatology, vol. 4, No. 2, pp. 212-218 (2006).
Oster, B. et al., "Identification and validation of highly frequent CpG island hypermethylation in colorectal adenomas and carcinomas." Int J Cancer. 2011;129(12):2855-66.
Person et al. "Chronic cadmium exposure in vitro induces cancer cell characteristics in human lung cells." Toxicol Appl Pharmacol. 2013; 273(2):281-8.
Petko Z., et al., "Aberrantly Methylated CDKN2A, MGMT, and MLH1 in Colon Polyps and in Fecal DNA from Patients with Colorectal Polyps." Clin Cancer Res 2005;11:1203-9.
Raimondo et al. "Methylated DNA Markers in Pancreatic Juice Discriminate Pancreatic Cancer From Chronic Pancreatitis and Normal Controls" Gastroenterology 2013; 144:S-90.
Rex et al. "American College of Gastroenterology guidelines for colorectal cancer screening 2008." Am J Gastroenterol (2009); 104, pp. 739-750.
Sadri and Hornsby "Rapid Analysis of DNA Methylation Using New Restriction Enzyme Sites Created by Bisulfite Modification." (1996) Nucl. Acids Res. 24: 5058-5059.
Sato et al., "Aberrant methylation of the HPP1 gene in ulcerative colitis-associated colorectal carcinoma." Cancer Res (2002), 62, pp. 6820-6822.
Sato, et al. (2003). "Discovery of novel targets of aberrant methylation in pancreatic carcinoma using high-throughput microarrays." Cancer Res. 63: 3735-3742.
Sato, et al. (2008). "CpG island methylation profile of pancreatic intraepithelial neoplasia." Mod Pathol. 21 93): 238-244.
Schulmann, et al., Molecular phenotype of inflammatory bowel disease-associated neoplasms with microsatellite instability, Gastroenterology, vol. 129, No. 1, pp. 74-85 (2005).
Seshagiri et al. "Recurrent R-spondin fusions in colon cancer." Nature. 2012; 488:660-4.
Shin et al. "Bile-based detection of extrahepatic cholangiocarcinoma with quantitative DNA methylation markers and its high sensitivity." The Journal of molecular diagnostics : JMD. 2012;14:256-63.
Singer-Sam et al. "A quantitative HpaII-PCR assay to measure methylation of DNA from a small number of cells" (1990) Nucl. Acids Res. 18(3): 687.
Singer-Sam et al. "A sensitive, quantitative assay for measurement of allele-specific transcripts differing by a single nucleotide." (1992) PCR Methods Appl. 1: 160-163.
Stumm et al. "Strong expression of the neuronal transcription factor FOXP2 is linked to an increased risk of early PSA recurrence in ERG fusion-negative cancers." Journal of clinical pathology. 2013;66:563-8.
Surdez et al. "Targeting the EWSR1-FLI1 oncogene-induced protein kinase PKC-beta abolishes ewing sarcoma growth." Cancer research. 2012;72:4494-503.
Szabo and Mann "Allele-specific expression and total expression levels of imprinted genes during early mouse development: implications for imprinting mechanisms." (1995) Genes Dev. 9(24): 3097-3108.
Tang, et al. (2010). "Prognostic significance of tissue factor pathway inhibitor 2 in pancreatic carcinoma and its effect on tumor invasion and metastatis." Med Oncol. 27: 867-875.

(56) References Cited

OTHER PUBLICATIONS

Taylor et al. "Expression of p53 in colorectal cancer and dysplasia complicating ulcerative colitis." Br J Surg (1993), 80, pp. 442-444.
Tonack, et al. (2009). "Pancreatic cancer: proteomic approaches to a challenging disease." Pancreatology. 9: 567-576.
Toyota, et al. (1999). "Identification of differentially methylated sequences in colorectal cancer by methylated CpG island amplification." Cancer Res. 59: 2307-2312.
Tsunoda, et al. (2009). "Methylation of CLDN6, FBN2, RBP1, RBP4, TFPI2 and TMEFF2 in esophageal squamous cell carcinoma." Oncol Rep. 21: 1067-1073.
Vincent et al. "Genome-wide analysis of promoter methylation associated with gene expression profile in pancreatic adenocarcinoma." Clinical cancer research : an official journal of the American Association for Cancer Research. 2011; 17:4341-54.
Watanabe, t., International Journal of Oncology (2011), 38, pp. 201-207.
Wheeler et al. "Hypermethylation of the promoter region of the E-cadherin gene (CDH1) in sporadic and ulcerative colitis associated colorectal cancer." Gut (2001), 48, pp. 367-371.
Wu, Gastroenterology (2011) 14: S-222.
Xiong, et al. (1997). Nucleic Acids Res. 25 (12): 2532-2534.
Yachida, et al. (2010). "Distant metastasis occurs late during the genetic evolution of pancreatic cancer." Nature. 467: 1114-1117.
Yamaguchi, et al. (2005). "Pancreatic juice cytology in intraductal papillary mucinous neoplasm of the pancreas." Pancreatology. 5: 416-421.
Yang N. et al. "Methylation markers for CCNA1 and C13ORF18 are strongly associated with high-grade cervical intraepithelial neoplasia and cervical cancer in cervical scrapings." Cancer epidemiology, biomarkers & prevention : a publication of the American Association for Cancer Research, cosponsored by the American Society of Preventive Oncology. 2009;18:3000-7.
Zhang et al. (2009). "DNA methylation analysis of chromosome 21 gene promoters at single base pair and single allele resolution." PLoS Genet. 5 (3): e1000438.
Zhao et al. "Genome-wide identification of Epstein-Barr virus-driven promoter methylation profiles of human genes in gastric cancer cells." Cancer. 2013;119:304-12.
Zou H., et al., "A Sensitive Method to Quantify Human Long DNA in Stool: Relevance to Colorectal Cancer Screening." Cancer Epidemiol Biomarkers Prev 2006;15:1115-9.
Zou H.Z., et al., "Detection of aberrant p16 methylation in the serum of colorectal cancer patients." Clin Cancer Res 2002;8(1):188-91.
Zou, et al. (2007). "Highly methylated genes in colorectal neoplasia: implications for screening." Cancer Epidemial Biomarkers Prev. 16: 2686-2696.
Zou, et al. (2009). "T2036 Pan-Detection of Gastrointestinal Neoplasms By Stool DNA Testing Establishment of Feasibility." Gastroenterology. 136: A-625.
Ahlquist et al., A Stool Collection Device: The First Step in Occult Blood Testing, Annals of Internal Medicine, 1988, 108(4):609-612.
Ahlquist et al., Molecular Stool Screening for Colorectal Cancer. Using DNA Markers May Be Beneficial, But Large Scale Evaluation is Needed. BMJ, 2000, 29;321:254-5.
Ahmed et al., Transcriptomic Molecular Markers for Screening Human Colon Cancer in Stool and Tissue, Cancer Genomics and Proteomics, 2007, 4:1-20.
Anderson et al. Aberrant Methylation During Gastric Carcinogenesis: Patterns of Acquisition Using Novel Methylated DNA Markers from Whole Methylome Discovery Gastroenterology Apr. 1, 2016;150(4):S863-S864.
Anderson et al., Methylated DNA Markers for Detection of Sporadic Colorectal Neoplasia: Comparison Between Age Groups Younger Than and Older Than 50. Abstract Su2013. Gastroenterology Apr. 1, 2016;150(4):S-611.
Andersson et al., Properties of targeted preamplification in DNA and cDNA quantification. Expert Rev Mol Diagn. 2015;15(8):1085-100.

Antequera et al., High levels of de novo methylation and altered chromatin structure at CpG islands in cell lines. Cell. Aug. 10, 1990;62(3):503-14.
Arneson et al., GenomePlex Whole-Genome Amplification. Cold Spring Harb. Protoc. 2008; doi:10.1101/pdb.prot4920, 7 pages.
Aronchick et al., A novel tableted purgative for colonoscopic preparation: Efficacy and safety comparisons with Colyte and Fleet Phospho-Soda. Gastrointestinal endoscopy, 2000;52:346-52.
Belshaw et al., Use of DNA from human stools to detect aberrant CpG island methylation of genes implicated in colorectal cancer. Cancer Epidemiol Biomarkers Prev. Sep. 2004;13(9):1495-501.
Berger et al., Stool DNA screening for colorectal neoplasia: biological and technical basis for high detection rates. Pathology 2012;44(2):80-8.
Bibikova, GoldenGate Assay for Methyltion of BeadArrayTM Technology. Jan. 1, 2009; retrieved from http://agtc.wayne.edu/pdfs/goldengate_methylation_brochure.pdf, retrieved Aug. 29, 2016, 7 pages.
Bonin et al., Identification of Differentially Methylated Regions in New Genes Associated with Knee Osteoarthritis. Gene. Jan. 15, 2016; 576(0): 312-318.
Bryson et al., Gene structure, sequence, and chromosomal localization of the human red cell-type low-molecular-weight acid phosphotyrosyl phosphatase gene, ACP1. Genomics. Nov. 20, 1995;30(2):133-40.
Budd et al., Circulating tumor cells versus imaging—predicting overall survival in metastatic breast cancer. Clin Cancer Res. Nov. 1, 2006;12(21):6403-9.
Bustin, Absolute quantification of mRNA using real-time reverse transcription polymerase chain reaction assays, J. Molecular Endocrinology, 2000, 25:169-193.
Ceska et al., Structure-specific DNA cleavage by 5' nucleases. Trends Biochem Sci. Sep. 1998;23(9):331-6.
Chamberlain et al., Deletion screening of the Duchenne muscular dystrophy locus via multiplex DNA amplification, Nucleic Acids Research, 1988, 16(23):11141-11156.
Chapman et al., Autoantibodies in lung cancer: possibilities for early detection and subsequent cure. Thorax. Mar. 2008;63(3):228-33.
Chen et al., Differential regulation of the human gene DAB2IP in normal and malignant prostatic epithelia: cloning and characterization. Genomics. Apr. 2002;79(4):573-81.
Chen et al., DNA Methylation Identifies Loci Distinguishing Hereditary Nonpolyposis Colorectal Cancer Without Germ-Line MLH1/MSH2 Mutation from Sporadic Colorectal Cancer. Clin Transl Gastroenterol. Dec. 15, 2016;7(12):e208. 12 pages.
Clayton et al., K-ras point mutation detection in lung cancer: comparison of two approaches to somatic mutation detection using ARMS allele-specific amplification. Clin Chem. Dec. 2000;46(12):1929-38.
Cohen et al., Relationship of circulating tumor cells to tumor response, progression-free survival, and overall survival in patients with metastatic colorectal cancer. J Clin Oncol. Jul. 1, 2008;26(19):3213-21.
Costello et al., Graded methylation in the promoter and body of the O6-methylguanine DNA methyltransferase (MGMT) gene correlates with MGMT expression in human glioma cells. J Biol Chem. Jun. 24, 1994;269(25):17228-37.
Crespi et al. Colorectal cancer: a spreading but preventable disease European Journal of Oncology. vol. 13(1). Mar. 2008. pp. 21-32.
Curriculum Vitae of Duncan H. Whitney, Ph.D., filed Jan. 11, 2024, 10 pages.
Dai et al., Global methylation profiling of lung cancer identifies novel methylated genes. Neoplasia. Jul.-Aug. 2001;3(4):314-23.
Dammann et al., The CpG island of the novel tumor suppressor gene RASSF1A is intensely methylated in primary small cell lung carcinomas. Oncogene. Jun. 14, 2001;20(27):3563-7.
Dasari et al., Trends in the Incidence, Prevalence, and Survival Outcomes in Patients With Neuroendocrine Tumors in the United States. JAMA Oncol. Oct. 1, 2017;3(10):1335-1342.
Dassonville et al., Expression of epidermal growth factor receptor and survival in upper aerodigestive tract cancer. J Clin Oncol. Oct. 1993;11(10):1873-8.

(56) References Cited

OTHER PUBLICATIONS

Davies et al., Somatic mutations of the protein kinase gene family in human lung cancer. Cancer Res. Sep. 1, 2005;65(17):7591-5.
Declaration of Brendan T. Jones, dated Jan. 11, 2024, 11 pages.
Declaration of Duncan Whitney, Ph.D., dated Jan. 10, 2024, 186 pages.
Derks et al., Promoter Methylation Precedes Chromosomal Alterations in Colorectal Cancer Development, Cellular Oncology, 2006, 28(5-6):247-257.
Deuter et al., A method for preparation of fecal DNA suitable for PCR. Nucleic Acids Res. Sep. 25, 1995;23(18):3800-1.
Dulak et al., Exome and whole-genome sequencing of esophageal adenocarcinoma identifies recurrent driver events and mutational complexity. Nat Genet. May 2013;45(5):478-86.
Egan. Signal Detection Theory and ROC Analysis, Academic Press, New York. 1975. TOC only. 9 pages.
Egeblad et al., New functions for the matrix metalloproteinases in cancer progression. Nat Rev Cancer. Mar. 2002;2(3):161-74.
Eguchi et al., Mutations of the P53 Gene in Stool of Patients with Resectable Colorectal Cancer, Cancer, 1996, 77(8):1707-1710.
Elbashir et al, RNA interference is mediated by 21- and 22-nucleotide RNAs. Genes Dev. Jan. 15, 2001;15(2):188-200.
Erlich (ed.), PCR Technology, Stockton Press. 1989. TOC only. 5 pages.
Etzioni et al., The case for early detection. Nat Rev Cancer. Apr. 2003;3(4):243-52.
Exact Sciences and Mount Sinai School of Medicine, Stool DNA Testing For Colon Cancer, Press Release issued Dec. 13, 2006, retrieved from https://www.sciencedaily.com/releases/2006/12/061213104115.htm#, on Jan. 9, 2024, 3 pages.
Fackler et al., Quantitative multiplex methylation-specific PCR assay for the detection of promoter hypermethylation in multiple genes in breast cancer. Cancer Res. Jul. 1, 2004;64(13):4442-52.
Fasman, Practical Handbook of Biochemistry and Molecular Biology, CRC Press, Boca Raton, FL. 1989, pp. 385-394.
Fearnhead et al., The ABC of APC, Hum. Mol. Genet. 2001, 10(7):721-733.
Fearon E., et al., A Genetic Model for Colorectal Tumorigenesis, Cell, 1990, 61:759-767.
Feil et al., Methylation analysis on individual chromosomes: improved protocol for bisulphite genomic sequencing. Nucleic Acids Res. Feb. 25, 1994;22(4):695-6.
Feliciano et al., miR-125b acts as a tumor suppressor in breast tumorigenesis via its novel direct targets ENPEP, CK2-α, CCNJ, and MEGF9, PLoS One. Oct. 3, 2013;8(10):e76247.
Finger et al., The wonders of flap endonucleases: structure, function, mechanism and regulation. Subcell Biochem. 2012;62:301-26.
Gardiner-Garden et al., CpG Islands in Vertebrate Genomes. J. Mol. Biol. 1987:196: 261-281.
Garrido-Laguna et al., Pancreatic cancer: from state-of-the-art treatments to promising novel therapies. Nat Rev Clin Oncol. Jun. 2015;12(6):319-34.
Gatlin et al., Automated identification of amino acid sequence variations in proteins by HPLC/microspray tandem mass spectrometry. Anal Chem. Feb. 15, 2000;72(4):757-63.
Gemperle et al., Regulation of the formyl peptide receptor 1 (FPR1) gene in primary human macrophages. PLoS One. 2012;7(11):e50195. 6 pages.
GenPept Accession No. NP05612. Sep. 11, 2022. 3 pages.
Gevaert et al., Pancancer analysis of DNA methylation-driven genes using MethylMix. Genome Biol. Jan. 29, 2015;16(1):17. 13 pages.
Grafstrom et al., The characteristics of DNA methylation in an in vitro DNA synthesizing system from mouse fibroblasts. Nucleic Acids Res. Apr. 25, 1985;13(8):2827-42.
Grandis et al., TGF-alpha and EGFR in Head and Neck Cancer. Journal of Cellular Biochemistry, 1993; Supplement 17f:188-191.
Greenman et al., Patterns of somatic mutation in human cancer genomes. Nature. Mar. 8, 2007;446(7132):153-8.

Grunau et al., Bisulfite genomic sequencing: systematic investigation of critical experimental parameters. Nucleic Acids Res. Jul. 1, 2001;29(13):E65-5. 7 pages.
Guittet et al., Comparison of a Guaiac Based and an Immunochemical Faecal Occult Blood Test In Screening For Colorectal Cancer In A General Average Risk Population, Gut, 2007, 56:210-214.
Hall et al., Sensitive detection of DNA polymorphisms by the serial invasive signal amplification reaction, PNAS, 2000, 97:8272.
Hallet et al., Exploring the rising incidence of neuroendocrine tumors: a population-based analysis of epidemiology, metastatic presentation, and outcomes. Cancer. Feb. 15, 2015;121(4):589-97.
Hanley et al., DNA integrity assay: a plasma-based screening tool for the detection of prostate cancer. Clin Cancer Res. Aug. 1, 2006;12(15):4569-74.
Harris et al., Single-molecule DNA sequencing of a viral genome. Science. Apr. 4, 2008;320(5872):106-9.
Haug et al., Mutant-enriched PCR and allele-specific hybridization reaction to detect K-ras mutations in stool DNA: high prevalence in a large sample of older adults. Clin Chem. Apr. 2007;53(4):787-90.
Haug et al., New stool tests for colorectal cancer screening: a systematic review focusing on performance characteristics and practicalness. Int J Cancer. Nov. 1, 2005;117(2):169-76.
Hayden et al., Multiplex-Ready PCR: A new method for multiplexed SSR and SNP genotyping, BMC Genomics, 2008, 9:80. 12 pages.
Heitman et al., Colorectal Cancer Screening for Average-Risk North Americans: An Economic Evaluation. PLoS Med, 2010;7(11):e1000370. 13 pages.
Heller et al., Lung cancer: from single-gene methylation to methylome profiling. Cancer Metastasis Rev. Mar. 2010;29(1):95-107.
Higuchi et al., A general method of in vitro preparation and specific mutagenesis of DNA fragments: study of protein and DNA interactions, Nucleic Acids Research, 1988, 16(15):7351-7367.
Higuchi et al., Kinetic PCR analysis: real-time monitoring of DNA amplification reactions, Biotechnology, 1993, 11:1026-1030.
Hiraoka, A. Leukemia cell lines require self-secreted stem cell growth factor (SCGF) for their proliferation. Leuk Res. Oct. 2008;32(10):1623-5.
Hiraoka, A., et al., Cloning, expression, and characterization of a cDNA encoding a novel human growth factor for primitive hematopoietic progenitor cells. Proc. Nat. Acad. Sci. 94: 7577-7582, 1997.
Hirata et al., Usefulness of Fecal Lactoferrin and Hemoglobin in Diagnosis of Colorectal Diseases, World Journal of Gastroenterology, 2007, 14;13(10):1569-74.
Hong, et al., Multiple genes are hypermethylated in intraductal papillary mucinous neoplasms of the pancreas. Mod Pathol. Dec. 2008;21(12):1499-507.
Horikoshi et al., Quantitative determination of the ratio of mutated to normal ras genes in the blood of leukemia patients by allele-specific PCR. Leuk Res. Sep. 1994;18(9):693-702.
Hua et al., Quantitative methylation analysis of multiple genes using methylation-sensitive restriction enzyme-based quantitative PCR for the detection of hepatocellular carcinoma. Exp Mol Pathol. Aug. 2011;91(1):455-60.
Huang et al., Transactivation of the epidermal growth factor receptor by formylpeptide receptor exacerbates the malignant behavior of human glioblastoma cells. Cancer Res. Jun. 15, 2007;67(12):5906-13.
Ito et al., Tet proteins can convert 5-methylcytosine to 5-formylcytosine and 5-carboxylcytosine. Science. Sep. 2, 2011;333(6047):1300-3.
Itzkowtiz et al., A Simplified, Noninvasive Stool DNA Test for Colorectal Cancer Detection, American Journal of Gastroenterology, 2008, 103:2862-2870.
Iyer et al., Accurate nonendoscopic detection of Barrett's esophagus by methylated DNA Markers: A multisite case control study. Am J Gastroenterol 2020;115:1201-1209.
Iyer et al., Accurate non-endoscopic detection of Barrett's esophagus in a multicenter prospective validation cohort: the sos 2 trial. AGA Abstracts. 2018:878. S-175-S-176.
Iyer et al., Highly Discriminant Methylated DNA Markers for the Non-endoscopic Detection of Barrett's Esophagus. Am J Gastroenterol. Aug. 2018;113(8):1156-1166.

(56) References Cited

OTHER PUBLICATIONS

Jessup et al., Diagnosing Colorectal Carcinoma: Clinical and Molecular Approaches, A Cancer Journal for Clinicians, 1997, 47(2):70-92.
Jiang et al., Lengthening and shortening of plasma DNA in hepatocellular carcinoma patients. Proc Natl Acad Sci U S A. Mar. 17, 2015;112(11):E1317-25.
Jongeneel et al., An atlas of human gene expression from massively parallel signature sequencing (MPSS) Genome Res. Jul. 2005;15(7):1007-14.
Jung et al., Gene silencing of TSPYL5 mediated by aberrant promoter methylation in gastric cancers. Lab. Invest. 88: 153-160, 2008.
Kacian et al., A replicating RNA molecule suitable for a detailed analysis of extracellular evolution and replication. Proc Natl Acad Sci U S A. Oct. 1972;69(10):3038-42.
Kahi et al., Screening, Surveillance, and Primary Prevention for Colorectal Cancer: A Review of the Recent Literature, Gastroenterology, 135:380-399 (2008).
Kaiser et al., A comparison of eubacterial and archaeal structure-specific 5'-exonucleases. J Biol Chem. Jul. 23, 1999;274(30):21387-94.
Kalinina et al., Nanoliter scale PCR with TaqMan detection, Nucleic Acids Research, 1997, 25:1999-2004.
Kanaoka et al., Potential Usefulness of Detecting Cyclooxygenase 2 Messenger RNA in Feces for Colorectal Cancer Screening, Gastroenterology, 127:422-427 (2004).
Karl et al., Improved Diagnosis of Colorectal Cancer Using a Combination of Fecal Occult Blood and Novel Fecal Protein Markers. Clin Gastroenterol Hepatol, 2008;6(10):1122-8.
Kastury, et al., E. Chromosome locations of human EMX and OTX genes. Genomics 22: 41-45, 1994.
Kinzler K., et al., Lessons from Hereditary Colorectal Cancer Cell, 1996, 87:159-170.
Kisiel et al., Hepatocellular Carcinoma Detection by Plasma Methylated DNA: Discovery, Phase I Pilot, and Phase II Clinical Validation. Hepatology. Mar. 2019;69(3):1180-1192.
Kisiel et al., Methylated eyes absent 4 (EYA4) gene promotor in non-neoplastic mucosa of ulcerative colitis patients with colorectal cancer: evidence for a field effect. Inflamm Bowel Dis. Sep. 2013;19(10):2079-83.
Kisiel et al., Novel Stool DNA Markers for Inflammatory Bowel Disease Asociated Colorectal Cancer High Grade Dysplasia: High Specificity Across Three Independent International Poplulations. Abstract 185. Gatroenterology 2016;150(4):S-48.
Kisiel, et al. Stool DNA screening for colorectal cancer: opportunities to improve value with next generation tests. J Clin Gastroenterol. 2011;45 (4): 301-8.
KLING. Ultrafast DNA sequencing. Nat Biotechnol. Dec. 2003;21(12):1425-7.
Koinuma et al., Screening for genomic fragments that are methylated specifically in colorectal carcinoma with a methylated MLH1 promoter. Carcinogenesis. Dec. 2005;26(12):2078-85.
Kraunz et al., Interaction between the bone morphogenetic proteins and Ras/MAP-kinase signalling pathways in lung cancer. Br J Cancer. Oct. 17, 2005;93(8):949-52.
Kristensen et al., PCR-based methods for detecting single-locus DNA methylation biomarkers in cancer diagnostics, prognostics, and response to treatment. Clin Chem. Aug. 2009;55(8):1471-83.
Kuppuswamy et al., Single nucleotide primer extension to detect genetic diseases: experimental application to hemophilia B (factor IX) and cystic fibrosis genes. Proc Natl Acad Sci U S A. Feb. 15, 1991;88(4):1143-7.
Kutzner et al., Non-Invasive Detection of Colorectal Tumours by the Combined Application Of Molecular Diagnosis and the Faecal Occult Blood Test, Cancer Letters, 229:33-41 (2005).
Lenhard et al., Analysis of promoter methylation in stool: a novel method for the detection of colorectal cancer. Clin Gastroenterol Hepatol. Feb. 2005;3(2):142-9.
Leung et al., Detection of Hypermethylated DNA or Cyclooxygenase-2 Messenger RNA in Fecal Samples of Patients with Colorectal Cancer or Polyps. Am J Gastroenterol 2007;102:1070-6.
Li et al., MethPrimer: designing primers for methylation PCRs. Bioinformatics. Nov. 2002;18(11):1427-31.
Li et al., Selection and Application of Tissue microRNAs for Nonendoscopic Diagnosis of Barrett's Esophagus. Gastroenterology. Sep. 2018;155(3):771-783.e3.
Lidgard et al., Clinical performance of an automated stool DNA assay for detection of colorectal neoplasia. Clin Gastroenterol Hepatol. Oct. 2013;11(10):1313-8.
LinkedIn Page of Joost Louwagie, retrieved from https://www.linkedin.com/in/joost-louwagie/?originalSubdomain=ch, on Jan. 10, 2024, 3 pages.
Lofton-Day et al., DNA methylation biomarkers for blood-based colorectal cancer screening. Clin Chem. Feb. 2008;54(2):414-23.
Loh et al. Bone Morphogenic Protein 3 Inactivation Is an Early and Frequent Event in Colorectal Cancer Development. Genes Chromosomes and Cancer. 2008, 47:449-460.
Louwagie et al., Feasibility of a DNA methylation assay for noninvasive CRC screening. Clin Cancer Res. Oct. 2007;13(19 Suppl):B16. 4 pages.
Lowe, et al., A computer program for selection of oligonucleotide primers for polymerase chain reactions. Nuc Acids Res 1990; 18(7): 1757-61.
Machiels et al., New protocol for DNA extraction of stool. Biotechniques. Feb. 2000;28(2):286-90.
Mahon, Prevention and Screening of Gastrointestinal Cancers, Seminars in Oncology Nursing, 25(1):15-31 (2009).
Maitra et al., Pancreatic cancer. Annu Rev Pathol. 2008;3:157-88.
Majumder et al., 596 Detection of Pancreatic High-Grade Dysplasia and Cancer using Novel Methylated DNA Markers: Discovery and Tissue Validation. Gastroenterology. 2016, 150(4):S120-S121.
Majumder et al., High Detection Rates of Pancreatic Cancer Across Stages by Plasma Assay of Novel Methylated DNA Markers and CA19-9. Clin Cancer Res. May 1, 2021;27(9):2523-2532.
Majumder et al., Novel DNA Methylation Markers Assayed from Cyst Fluid Accurately Detect Advanced Neoplasia in Pancreatic Cysts: A Multicenter Study. Gastroenterology. 2017, 152(5):S148.
Mandal et al., Lipopolysaccharide induces formyl peptide receptor 1 gene expression in macrophages and neutrophils via transcriptional and posttranscriptional mechanisms. J Immunol. Nov. 1, 2005;175(9):6085-91.
Mandal et al., Signaling in lipopolysaccharide-induced stabilization of formyl peptide receptor 1 mRNA in mouse peritoneal macrophages. J Immunol. Feb. 15, 2007;178(4):2542-8.
Margulies et al., Genome sequencing in microfabricated high-density picolitre reactors. Nature. Sep. 15, 2005;437(7057):376-80.
Matsumura et al., Non-Invasive Detection of Malignancy by Identification of Unusual CD44 Gene Activity in Exfoliated Cancer Cells, BMJ, 308:619-624 (1994).
Matsumura et al., Significance of CD44 Gene Products for Cancer Diagnosis and Disease Evaluation, Lancet, 340:1053-1058 (1992).
Matsushita et al., DNA-friendly Cu(ii)/TEMPO-catalyzed 5-hydroxymethylcytosine-specific oxidation. Chem Commun (Camb). May 23, 2017;53(42):5756-5759.
Medina-Aguilar et al., Methylation Landscape of Human Breast Cancer Cells in Response to Dietary Compound Resveratrol. PLoS One. Jun. 29, 2016;11(6):e0157866. 20 pages.
Meissner et al., Reduced representation bisulfite sequencing for comparative high- resolution DNA methylation analysis. Nucleic Acids Res. Oct. 13, 2005;33(18):5868-77.
Melnikov et al., MSRE-PCR for analysis of gene-specific DNA methylation. Nucleic Acids Res. Jun. 8, 2005;33(10):e93.
Melvin and Brooke, Laboratory Procedures for the Diagnosis of Intestinal Parasites, Third Edition, 1982, published by U.S. Department of Health and Human Services, Centers for Disease Control, Atlanta, Georgia, 284 pages.
Mercer, Use of multiple markers to enhance clinical utility. Immunol Ser. 1990:53:39-54.
Mitchell et al., A panel of genes methylated with high frequency in colorectal cancer. BMC Cancer. Jan. 31, 2014;14:54. 15 pages.

(56) References Cited

OTHER PUBLICATIONS

Mitchell et al., Evaluation of Methylation Biomarkers for Detection of Circulating Tumor DNA and Application to Colorectal Cancer. Genes (Basel). Dec. 15, 2016;7(12):125. 11 pages.
Modiano et al., Risk factors for the detection of Barrett's esophagus in patients with erosive esophagitis. Gastrointest Endosc. May 2009;69(6):1014-20.
Moinova et al., Identifying DNA methylation biomarkers for non-endoscopic detection of Barrett's esophagus. Sci Transl Med. Jan. 17, 2018;10(424):eaao5848.
Monte et al., Cloning, chromosome mapping and functional characterization of a human homologue of murine gtse-1 (B99) gene. Gene. Aug. 22, 2000;254(1-2):229-36.
Monte et al., hGTSE-1 expression stimulates cytoplasmic localization of p53. J Biol Chem. Mar. 19, 2004;279(12):11744-52.
Montiero et al., Complex polysaccharides as PCR inhibitors in feces: Helicobacter pylori model. J Clin Microbiol. Apr. 1997;35(4):995-8.
Munson et al., Recovery of bisulfite-converted genomic sequences in the methylation-sensitive QPCR. Nucleic Acids Res. 2007;35(9):2893-903.
Naruse et al., Fecal pancreatic elastase: a reproducible marker for severe exocrine pancreatic insufficiency. J Gastroenterol. Sep. 2006;41(9):901-8.
Nechvatal et al., Fecal Collection, Ambient Preservation, and DNA Extraction for PCR Amplification of Bacterial And Human Markers from Human Feces, Journal of Microbiological Methods, 72(2):124-32 (2008).
Nelson et al., k-ras mutation and occupational asbestos exposure in lung adenocarcinoma: asbestos-related cancer without asbestosis. Cancer Res. Sep. 15, 1999;59(18):4570-3.
Neuwelt et al., Possible sites of origin of human plasma ribonucleases as evidenced by isolation and partial characterization of ribonucleases from several human tissues. Cancer Res. Jan. 1978;38(1):88-93.
Nishikawa et al., A Simple Method Of Detecting K-Ras Point Mutations in Stool Samples for Colorectal Cancer Screening Using One-Step Polymerase Chain Reaction/Restriction Fragment Length Polymorphism Analysis, Clinica Chimica Acta, 318:107-112 (2002).
Nyce et al. Variable effects of DNA-synthesis inhibitors upon DNA methylation in mammalian cells. Nucleic Acids Res. 1986;14:4353-4367.
O'Driscoll et al., Feasibility and relevance of global expression profiling of gene transcripts in serum from breast cancer patients using whole genome microarrays and quantitative RT-PCR. Cancer Genomics Proteomics. Mar.-Apr. 2008;5(2):94-104.
Oh et al., Genome-wide identification and validation of novel mehylation biomarker, SDC2, for blood-based detection of colorectal cancer. J Mol Diagn. Jul. 2013;15(4):498-507.
Okamoto et al., 5-Hydroxymethylcytosine-selective oxidation with peroxotungstate. Chem Commun (Camb). Oct. 28, 2011;47(40):11231-3.
Olek et al., A modified and improved method for bisulphite based cytosine methylation analysis. Nucleic Acids Res. Dec. 15, 1996;24(24):5064-6.
Olivier, The Invader assay for SNP genotyping, Mutat Res. Jun. 3, 2005;573(1-2):103-10.
Olkhov-Mitsel et al., Novel multiplex MethyLight protocol for detection of DNA methylation in patient tissues and bodily fluids. Sci Rep. Mar. 21, 2014;4:4432.
Orpana, Fluorescence resonance energy transfer (FRET) using ssDNA binding fluorescent dye, Biomol Eng. Apr. 2004;21(2):45-50.
Ostrow, Tests for Fecal Occult Blood, Chapter 98 in Clinical Methods: The History, Physical, and Laboratory Examinations. Third Edition, eds. Walker et al, Boston: Butterworths, 3 pages (1990).
Ota et al., Complete sequencing and characterization of 21,243 full-length human cDNAs. Nat Genet. Jan. 2004;36(1):40-5.

Raimondo, M. et al. Sensitive DNA Marker Panel for Detection of Pancreatic Cancer by Assay in Pancreatic Juice, Gastroenterology, May 2, 2014, vol. 146, Iss. 5, Suppl. 1, p. S-132.
Reddi et al., Elevated serum ribonuclease in patients with pancreatic cancer. Proc Natl Acad Sci U S A. Jul. 1976;73(7):2308-10.
Rein et al., Identifying 5-methylcytosine and related modifications in DNA genomes. Nucleic Acids Res. May 15, 1998;26(10):2255-64.
Reinartz et al., Massively parallel signature sequencing (MPSS) as a tool for in-depth quantitative gene expression profiling in all organisms. Brief Funct Genomic Proteomic. Feb. 2002;1(1):95-104.
Ren et al., Discovery and development of differentially methylated regions in human papillomavirus-related oropharyngeal squamous cell carcinoma. Int J Cancer. Nov. 15, 2018;143(10):2425-2436.
Rennert et al., Detecting K-Ras Mutations in Stool from Fecal Occult Blood Test Cards in Multiphasic Screening for Colorectal Cancer, Cancer Letters, 253:258-264 (2007).
Rex et al., American College of Gastroenterology Guidelines for Colorectal Cancer Screening 2008. Am J Gastroenterol, 2009;104:739-50.
Robertson et al., The presence of 5-hydroxymethylcytosine at the gene promoter and not in the gene body negatively regulates gene expression. Biochem Biophys Res Commun. Jul. 22, 2011;411(1):40-3.
Ronaghi et al., Real-time DNA sequencing using detection of pyrophosphate release. Anal Biochem. Nov. 1, 1996;242(1):84-9.
Ross-Innes et al., Evaluation of a minimally invasive cell sampling device coupled with assessment of trefoil factor 3 expression for diagnosing Barrett's esophagus: a multi-center case-control study. PLoS Med. Jan. 29, 2015;12(1):e1001780.
Rothberg et al., An integrated semiconductor device enabling non-optical genome sequencing. Nature. Jul. 20, 2011;475(7356):348-52.
Roux, Using mismatched primer-template pairs in touchdown PCR, Biotechniques, 1994, 16(5):812-814.
Salomon et al., Methylation of mouse DNA in vivo: di- and tripyrimidine sequences containing 5-methylcytosine. Biochim Biophys Acta. Apr. 15, 1970;204(2):340-51.
Santini et al., Characterization, quantification, and potential clinical value of the epidermal growth factor receptor in head and neck squamous cell carcinomas. Head & Neck, 1991; 13(2): 132-139.
Sato et al., Hypermethylation of the p14(ARF) gene in ulcerative colitis-associated colorectal carcinogenesis. Cancer Res. Feb. 15, 2002;62(4):1148-51.
Sawas et al., Eradication of Dysplasia Only Without Eradicating Intestinal Metaplasia is Associated With Higher Risk of Advance Neoplasia Recurrence: Meta-Analysis. Abstract 8, Gastroenterology. 2018; 15(6)Suppl 1:S-3.
Sawas et al., The Main Effect of Endoscopic Barrett's Therapy is in the Eradicating Prevalent and Not Recurrent Neoplasia: Meta-Anlaysis. Abstract7, Gastroenterology. 2018; 15(6)Suppl 1:S-2 and S-3.
Schouten et al., Relative quantification of 40 nucleic acid sequences by multiplex ligation-dependent probe amplification, Nucleic Acids Research, 2002, 30(12): e57. 13 pages.
Schuebel et al., Comparing the DNA hypermethylome with gene mutations in human colorectal cancer. PLoS Genet. Sep. 2007;3(9):1709-23.
Schuuring et al., Identification and cloning of two overexpressed genes, U21B31/PRAD1 and EMS1, within the amplified chromosome 11q13 region in human carcinomas. Oncogene. Feb. 1992;7(2):355-61.
Selvin, Fluorescence resonance energy transfer, 1995, Methods Enzymol. 1995;246:300-34.
Shao et al., Formyl peptide receptor ligands promote wound closure in lung epithelial cells. Am J Respir Cell Mol Biol. Mar. 2011;44(3):264-9.
Shen et al., Integrated Genetic and Epigenetic Analysis Identifies Three Different Subclasses of Colon Cancer. Proc Natl. Acad. Sci. U.S.A., 104(47): 18654-18659 (2007).
Shen et al. Integrative epigenomic and genomic filtering for methylation markers in hepatocellular carcinomas. BMC Med Genomics. Jun. 10, 2015;8:28, pp. 1-12.

(56) References Cited

OTHER PUBLICATIONS

Shendure et al., Next-generation DNA sequencing. Nat Biotechnol. Oct. 2008;26(10):1135-45.
Shimada et al., Pancreatic elastase IIIA and its variants are expressed in pancreatic carcinoma cells. Int J Mol Med. Nov. 2002;10(5):599-603.
Sidransky, Identification of ras Oncogene Mutations in the Stool of Patients with Curable Colorectal Tumors, Science, 256:102-105 (1992).
Siegel et al., Cancer Statistics, 2013. CA Cancer J Clin. 2013;63:11-30.
Simon, Occult Blood Screening for Colorectal Carcinoma: A Critical Review, Gastroenterology, 88:820837 (1985).
Siravegna et al., How liquid biopsies can change clinical practice in oncology. Ann Oncol. Oct. 1, 2019;30(10):1580-159.
Sjoblom et al., The consensus coding sequences of human breast and colorectal cancers. Science. Oct. 13, 2006;314(5797):268-74.
Soussi et al., p53 mutation heterogeneity in cancer. Biochem Biophys Res Commun. Jun. 10, 2005;331(3):834-42.
Spitzwieser et al., Promoter methylation patterns of ABCB1, ABCC1 and ABCG2 in human cancer cell lines, multidrug-resistant cell models and tumor, tumor-adjacent and tumor-distant tissues from breast cancer patients. Oncotarget. Nov. 8, 2016;7(45):73347-73369.
Stephens et al., A screen of the complete protein kinase gene family identifies diverse patterns of somatic mutations in human breast cancer. Nat Genet. Jun. 2005;37(6):590-2. doi: 10.1038/ng1571. Epub May 22, 2005.
Straub et al., Base5, a versatile, highly integrated high-throughput methylation profiling for methylation specific PCR based marker identification applied to colorectal cancer. Clin Cancer Res. Oct. 2007; 13(19 Suppl):A61. 4 pages.
Stryer, Fluorescence energy transfer as a spectroscopic ruler, Annu Rev Biochem. 1978;47:819-46.
Sun XJ, et al. An integrated analysis of genome-wide DNA methylation and gene expression data in hepatocellular carcinoma. FEBS Open Bio. May 30, 2018;8(7):1093-1103.
Szabo et al., Allele-specific expression and total expression levels of imprinted genes during early mouse development: implications for imprinting mechanisms. Genes Dev. Dec. 15, 1995;9(24):3097-108.
Tagore et al. Review Article: The Evolution to Stool DNA Testing for Colorectal Cancer, Aliment Pharmacol. Ther., 19:1225-1233 (2004).
Toth et al, Detection of methylated SEPT9 in plasma is a reliable screening method for both left- and right-sided colon cancers. PLoS One. 2012;7(9):e46000.
Triglia et al., A procedure for in vitro amplification of DNA segments that lie outside the boundaries of known sequences, Nucleic Acids Res., 1988, 16:8186.
Tsou et al., Identification of a panel of sensitive and specific DNA methylation markers for lung adenocarcinoma. Mol Cancer. Oct. 29, 2007:6:70.
Turcatti et al., A new class of cleavable fluorescent nucleotides: synthesis and optimization as reversible terminators for DNA sequencing by synthesis. Nucleic Acids Res. Mar. 2008;36(4):e25. 13 pages.
Türeci et al., Humoral immune responses of lung cancer patients against tumor antigen NY-ESO-1. Cancer Lett. May 8, 2006;236(1):64-71.
Turner et al., Role of matrix metalloproteinase 9 in pituitary tumor behavior. J Clin Endocrinol Metab. Aug. 2000;85(8):2931-5.
Vancompernolle et al., Expression and function of formyl peptide receptors on human fibroblast cells. J Immunol. Aug. 15, 2003;171(4):2050-6.
Vilkin et al., Performance Characteristics and Evaluation of an Automated-Developed and Quantitative, Immunochemical Fecal Occult Blood Screening Test, American Journal of Gastroenterology, 100:2519-2525 (2005).
Villa et al., Identification of Subjects at Risk for Colorectal Carcinoma through a Test Based on K-Ras Determination in the Stool, Gastroenterology, 110:1346-1353 (1996).
Vogelstein et al. Digital PCR. Proc Natl Acad Sci USA. 1999;96; 9236-41.
Wang et al., Crosstalk to stromal fibroblasts induces resistance of lung cancer to epidermal growth factor receptor tyrosine kinase inhibitors. Clin Cancer Res. Nov. 1, 2009;15(21):6630-8.
Wang et al., Usefulness of p53 gene mutations in the supernatant of bile for diagnosis of biliary tract carcinoma: comparison with K-ras mutation. J Gastroenterol. 2002;37(10):831-9.
Wasserkort et al., Aberrant septin 9 DNA methylation in colorectal cancer is restricted to a single CpG island. BMC Cancer. Aug. 30, 2013:13:398.
White et al., Colorectal Cancer: Prevention and Early Diagnosis, Medicine, 35(6):297-301 (2007).
Wilm et al., Femtomole sequencing of proteins from polyacrylamide gels by nano-electrospray mass spectrometry. Nature. Feb. 1, 1996;379(6564):466-9.
Wo et al. Sequencing, cloning, and expression of human red cell-type acid phosphatase, a cytoplasmic phosphotyrosyl protein phosphatase. J. Biol. Chem. 267:10856-10865, 1992.
Wood et al., The genomic landscapes of human breast and colorectal cancers. Science. Nov. 16, 2007;318(5853):1108-13.
Woodcock et al., The majority of methylated deoxycytidines in human DNA are not in the CpG dinucleotide. Biochem. Biophys. Res. Commun. 1987; 145: 888-894.
Wu et al., The ligation amplification reaction (LAR)—amplification of specific DNA sequences using sequential rounds of template-dependent ligation. Genomics. May 1989;4(4):560-9.
Xiong, et al., COBRA: a sensitive and quantitative DNA methylation assay. Nucleic Acids Res. Jun. 15, 1997;25(12):2532-4.
Yano, M., et al. Aberrant promoter methylation of human DAB2 interactive protein (hDAB2IP) gene in lung cancers. Int. J. Cancer 113: 59-66, 2005.
Yi et al., Novel methylation biomarker panel for the early detection of pancreatic cancer. Clin Cancer Res. Dec. 1, 2013;19(23):6544-6555.
Yoo et al., Epigenetic therapy of cancer: past, present and future. Nat Rev Drug Discov. Jan. 2006;5(1):37-50.
Young et al., New Stool Screening Tests for Colorectal Cancer, Digestion, 76:26-33 (2007).
Yu et al., Significance of combined detection of LunX mRNA and tumor markers in diagnosis of lung carcinoma. Chin J Cancer Res. Feb. 2014;26(1):89-94.
Zeschnigk et al., Imprinted segments in the human genome: different DNA methylation patterns in the Prader-Willi/Angelman syndrome region as determined by the genomic sequencing method. Hum Mol Genet. Mar. 1997;6(3):387-95.
Zha et al., Overexpression of HOXA1 correlates with poor prognosis in patients with hepatocellular carcinoma Tumour Biol. Dec. 2012;33(6):2125-34. Epub Aug. 4, 2012.
Zhang et al., Low expression of DAB2IP contributes to malignant development and poor prognosis in hepatocellular carcinoma. J. Gastroenterol Hepatol. Jun. 2012;27(6):1117-25.
Zhou et al., Massively parallel signature sequencing. Methods Mol Biol. 2006;331:285-311.
Zou et al., Quantification of methylated markers with a multiplex methylation-specific technology. Clin Chem. Feb. 2012;58(2):375-83.
Zou et al., Sensitive quantification of methylated markers with a novel methylation specific technology. Abstract D-144, Clin Chem 2010;56(6)Suppl:A199. 3 pages.
Certified U.S. Appl. No. 60/900,713, filed Feb. 12, 2007, in the name of Baylin et al., 188 pages.
CN Office Action for CN Patent Application No. 201480015389.5, mailed Mar. 30, 2018, 6 pages.
Declaration of Mr. Anthony P. Shuber, MS, Reexam U.S. Appl. No. 90/015,237, filed May 22, 2023, 63 pages.
EP Search Report for EP 16773766.7, dated Jan. 22, 2019, 4 pages.
Extended European Search Report for EP 21788930.2, mailed Mar. 15, 2024, 8 pages.

(56) References Cited

OTHER PUBLICATIONS

EP Search Report, EP Patent Application No. 15772326.3, mailed Nov. 28, 2017.
International Search Report and Written Opinion for Int'l Patent Application PCT/US2014/024582, mailed Sep. 24, 2014, 23 pages.
International Search Report and Written Opinion for Int'l Patent Application PCT/US2014/024589, mailed Sep. 29, 2014, 23 pages.
International Search Report and Written Opinion for PCT/US2020/026581. Mailed Aug. 31, 2020. 24 pages.
International Search Report and Written Opinion for PCT/US2021/030635. Mailed Oct. 26, 2021. 32 pages.
International Search Report and Written Opinion for PCT/US2022/079270, mailed Feb. 22, 2023, 24 pages.
International Search Report and Written Opinion for PCT/US2023/085117, mailed Apr. 29, 2024, 14 pages.
Supplementary Partial European Search Report, EP Application No. 14776150.6, mailed Jan. 3, 2017, 19 pages.
Supplementary Partial European Search Report, EP Patent Application No. 17847642.0, mailed Oct. 7, 2020, 14 pages.
Supplementary European Search Report for EP20782990. Mailed Feb. 21, 2022. 11 pages.
USPTO Final Office Action for US Patent Publication No. US15/010,436 dated Oct. 28, 2016, 15 pages.
Recorded Assignment of U.S. Pat. No. 11,634,781 dated Apr. 25, 2017, 5 pages.
USPTO Nonfinal Office Action for US Patent Publication No. US17/936,335 dated Jan. 11, 2023, 7 pages.
USPTO Order Granting Request for Ex Parte Reexamination of U.S. Pat. No. 11,634,781 dated Jun. 29, 2023, 18 pages.
USPTO Notice of Intent to Issue Ex Parte Reexamination Certificate for U.S. Pat. No. 11,634,781 dated Oct. 18, 2023, 5 pages.
Ex Parte Reexamination Certificate for U.S. Pat. No. 11,637,781, issued Dec. 4, 2023, 2 pages.
Petition for Inter Parties Review of U.S. Pat. No. 11,634,781, filed Jan. 11, 2024, 87 pages.
U.S. Appl. No. 61/149,581, filed Feb. 3, 2009, 59 pages.
Provisional Patent Application Transmittal for U.S. Appl. No. 61/149,581, dated Feb. 3, 2009, 3 pages.

* cited by examiner

SEQUENCE LISTING

<160> NUMBER OF SEQ ID NOS: 44

<210> SEQ ID NO 1
<211> LENGTH: 25
<212> TYPE: DNA
<213> ORGANISM: artificial sequence
<220> FEATURE:
<223> OTHER INFORMATION: Artificial DNA primer

<400> SEQUENCE: 1 ggtttttgg ttatttcgga atcgt                                    25

<210> SEQ ID NO 2
<211> LENGTH: 25
<212> TYPE: DNA
<213> ORGANISM: artificial sequence
<220> FEATURE:
<223> OTHER INFORMATION: Artificial DNA primer

<400> SEQUENCE: 2
tataaaaacg cgcgtaatca acgct                                   25

```
<210> SEQ ID NO 3
<211> LENGTH: 31
<212> TYPE: DNA
<213> ORGANISM: artificial sequence
<220> FEATURE:
<223> OTHER INFORMATION: Artificial DNA primer

<400> SEQUENCE: 3
cgggttttag cgatgtttat tttagtttcg t                           31

<210> SEQ ID NO 4
<211> LENGTH: 26
<212> TYPE: DNA
<213> ORGANISM: artificial sequence
<220> FEATURE:
<223> OTHER INFORMATION: Artificial DNA primer

<400> SEQUENCE: 4 cctttcgtt cgtataaaat ttcgtt                                  26

<210> SEQ ID NO 5
<211> LENGTH: 25
<212> TYPE: DNA
<213> ORGANISM: artificial sequence
<220> FEATURE:
<223> OTHER INFORMATION: Artificial DNA primer

<400> SEQUENCE: 5
tgggttatcg gttttttaag ttcgg                                  25

<210> SEQ ID NO 6
<211> LENGTH: 26
<212> TYPE: DNA
<213> ORGANISM: artificial sequence
<220> FEATURE:
<223> OTHER INFORMATION: Artificial DNA primer

<400> SEQUENCE: 6
gaattcctcc caaccaaccc tctacg                                 26

<210> SEQ ID NO 7
<211> LENGTH: 34
<212> TYPE: DNA
<213> ORGANISM: artificial sequence
<220> FEATURE:
<223> OTHER INFORMATION: Artificial DNA primer

<400> SEQUENCE: 7
tagtacgttt aggtaattgt ttaggtttag tcgt                        34

<210> SEQ ID NO 8
<211> LENGTH: 19
<212> TYPE: DNA
<213> ORGANISM: artificial sequence
<220> FEATURE:
<223> OTHER INFORMATION: Artificial DNA primer

<400> SEQUENCE: 8
cgaaaaccca actcccgaa                                         19

<210> SEQ ID NO 9
<211> LENGTH: 25
<212> TYPE: DNA
<213> ORGANISM: artificial sequence
<220> FEATURE:
<223> OTHER INFORMATION: Artificial DNA primer
```

```
<400> SEQUENCE: 9
ggtagtgttt tttcgagacg cggtc                                          25

<210> SEQ ID NO 10
<211> LENGTH: 20
<212> TYPE: DNA
<213> ORGANISM: artificial sequence
<220> FEATURE:
<223> OTHER INFORMATION: Artificial DNA primer

<400> SEQUENCE: 10
gatacgcgaa cacgcacacg                                                20

<210> SEQ ID NO 11
<211> LENGTH: 24
<212> TYPE: DNA
<213> ORGANISM: artificial sequence
<220> FEATURE:
<223> OTHER INFORMATION: Artificial DNA primer

<400> SEQUENCE: 11
gtttttcgtt gagttagaag cgtt                                           24

<210> SEQ ID NO 12
<211> LENGTH: 24
<212> TYPE: DNA
<213> ORGANISM: artificial sequence
<220> FEATURE:
<223> OTHER INFORMATION: Artificial DNA primer

<400> SEQUENCE: 12
acctcaatat aaataaaaac gcaa                                           24

<210> SEQ ID NO 13
<211> LENGTH: 24
<212> TYPE: DNA
<213> ORGANISM: artificial sequence
<220> FEATURE:
<223> OTHER INFORMATION: Artificial DNA primer

<400> SEQUENCE: 13
gtcgtttttg ggcgttttag aggc                                           24

<210> SEQ ID NO 14
<211> LENGTH: 20
<212> TYPE: DNA
<213> ORGANISM: artificial sequence
<220> FEATURE:
<223> OTHER INFORMATION: Artificial DNA primer

<400> SEQUENCE: 14
taatcccaaa cgaaccgccg                                                20

<210> SEQ ID NO 15
<211> LENGTH: 30
<212> TYPE: DNA
<213> ORGANISM: artificial sequence
<220> FEATURE:
<223> OTHER INFORMATION: Artificial DNA primer

<400> SEQUENCE: 15
cgggggtaaa aagggtagcg atagtgatac                                     30

<210> SEQ ID NO 16
```

```
<211> LENGTH: 23
<212> TYPE: DNA
<213> ORGANISM: artificial sequence
<220> FEATURE:
<223> OTHER INFORMATION: Artificial DNA primer

<400> SEQUENCE: 16
cgaaaaattc gaaacgaaac gtc                                           23

<210> SEQ ID NO 17
<211> LENGTH: 26
<212> TYPE: DNA
<213> ORGANISM: artificial sequence
<220> FEATURE:
<223> OTHER INFORMATION: Artificial DNA primer

<400> SEQUENCE: 17
cggttgttta acgagaaaga gatcgt                                        26

<210> SEQ ID NO 18
<211> LENGTH: 25
<212> TYPE: DNA
<213> ORGANISM: artificial sequence
<220> FEATURE:
<223> OTHER INFORMATION: Artificial DNA primer

<400> SEQUENCE: 18
gatctaattc ctcctccacg ccgta                                         25

<210> SEQ ID NO 19
<211> LENGTH: 31
<212> TYPE: DNA
<213> ORGANISM: artificial sequence
<220> FEATURE:
<223> OTHER INFORMATION: Artificial DNA primer

<400> SEQUENCE: 19
cgcggtgagt ttagttattg attttttaacg g                                 31

<210> SEQ ID NO 20
<211> LENGTH: 23
<212> TYPE: DNA
<213> ORGANISM: artificial sequence
<220> FEATURE:
<223> OTHER INFORMATION: Artificial DNA primer

<400> SEQUENCE: 20
aacgtccaaa acgcccaaac gta                                           23

<210> SEQ ID NO 21
<211> LENGTH: 25
<212> TYPE: DNA
<213> ORGANISM: artificial sequence
<220> FEATURE:
<223> OTHER INFORMATION: Artificial DNA primer

<400> SEQUENCE: 21
gttttatagg ttagcgtcga gtcga                                         25

<210> SEQ ID NO 22
<211> LENGTH: 25
<212> TYPE: DNA
<213> ORGANISM: artificial sequence
<220> FEATURE:
<223> OTHER INFORMATION: Artificial DNA primer

<400> SEQUENCE: 22
```
atctatcgcc gattacaaaa tcgaa                                         25

<210> SEQ ID NO 23
<211> LENGTH: 26
<212> TYPE: DNA
<213> ORGANISM: artificial sequence
<220> FEATURE:
<223> OTHER INFORMATION: Artificial DNA primer

<400> SEQUENCE: 23
gggggtaggg aaggaatatt ttcgtc                                       26

<210> SEQ ID NO 24
<211> LENGTH: 25
<212> TYPE: DNA
<213> ORGANISM: artificial sequence
<220> FEATURE:
<223> OTHER INFORMATION: Artificial DNA primer

<400> SEQUENCE: 24
gacgcccctc tcaattaaac aatcg                                        25

<210> SEQ ID NO 25
<211> LENGTH: 23
<212> TYPE: DNA
<213> ORGANISM: artificial sequence
<220> FEATURE:
<223> OTHER INFORMATION: Artificial DNA primer

<400> SEQUENCE: 25 gtttaattttt cggtttcgtc gtc                                         23

<210> SEQ ID NO 26
<211> LENGTH: 18
<212> TYPE: DNA
<213> ORGANISM: artificial sequence
<220> FEATURE:
<223> OTHER INFORMATION: Artificial DNA primer

<400> SEQUENCE: 26
cgctacgaaa cactccga                                                18

<210> SEQ ID NO 27
<211> LENGTH: 34
<212> TYPE: DNA
<213> ORGANISM: artificial sequence
<220> FEATURE:
<223> OTHER INFORMATION: Artificial DNA primer

<400> SEQUENCE: 27
tttcgtcgtt cgttattaag ggttatttttt agac                             34

<210> SEQ ID NO 28
<211> LENGTH: 20
<212> TYPE: DNA
<213> ORGANISM: artificial sequence
<220> FEATURE:
<223> OTHER INFORMATION: Artificial DNA primer

<400> SEQUENCE: 28
atcacgacgc tacacccgac                                              20

<210> SEQ ID NO 29
<211> LENGTH: 30
<212> TYPE: DNA

<213> ORGANISM: artificial sequence
<220> FEATURE:
<223> OTHER INFORMATION: Artificial DNA primer

<400> SEQUENCE: 29
ttagtagtaa attttttttgg tttagggcgt                     30

<210> SEQ ID NO 30
<211> LENGTH: 25
<212> TYPE: DNA
<213> ORGANISM: artificial sequence
<220> FEATURE:
<223> OTHER INFORMATION: Artificial DNA primer

<400> SEQUENCE: 30
aaaactatcc gaccgcgaat acgaa                           25

<210> SEQ ID NO 31
<211> LENGTH: 27
<212> TYPE: DNA
<213> ORGANISM: artificial sequence
<220> FEATURE:
<223> OTHER INFORMATION: Artificial DNA primer

<400> SEQUENCE: 31
ttgtaagcgg ttatagtatt attacgg                         27

<210> SEQ ID NO 32
<211> LENGTH: 20
<212> TYPE: DNA
<213> ORGANISM: artificial sequence
<220> FEATURE:
<223> OTHER INFORMATION: Artificial DNA primer

<400> SEQUENCE: 32
taatccccgc gattcccgaa                                 20

<210> SEQ ID NO 33
<211> LENGTH: 30
<212> TYPE: DNA
<213> ORGANISM: artificial sequence
<220> FEATURE:
<223> OTHER INFORMATION: Artificial DNA primer

<400> SEQUENCE: 33
ggcgtaattg ttgggaaacg taaagtattc                      30

<210> SEQ ID NO 34
<211> LENGTH: 23
<212> TYPE: DNA
<213> ORGANISM: artificial sequence
<220> FEATURE:
<223> OTHER INFORMATION: Artificial DNA primer

<400> SEQUENCE: 34
gaccaaaaaa acgccgctac gct                             23

<210> SEQ ID NO 35
<211> LENGTH: 24
<212> TYPE: DNA
<213> ORGANISM: artificial sequence
<220> FEATURE:
<223> OTHER INFORMATION: Artificial DNA primer

<400> SEQUENCE: 35
cgtcgcggaa tttagggatt aacg                            24

<210> SEQ ID NO 36
<211> LENGTH: 23
<212> TYPE: DNA
<213> ORGANISM: artificial sequence
<220> FEATURE:
<223> OTHER INFORMATION: Artificial DNA primer

<400> SEQUENCE: 36
ataccaaaac tcgcacctac gac                                    23

<210> SEQ ID NO 37
<211> LENGTH: 25
<212> TYPE: DNA
<213> ORGANISM: artificial sequence
<220> FEATURE:
<223> OTHER INFORMATION: Artificial DNA primer

<400> SEQUENCE: 37
tattttatag tcgcgttaaa agcgt                                  25

<210> SEQ ID NO 38
<211> LENGTH: 25
<212> TYPE: DNA
<213> ORGANISM: artificial sequence
<220> FEATURE:
<223> OTHER INFORMATION: Artificial DNA primer

<400> SEQUENCE: 38
gtcgataaaa aacctacgcg acgaa                                  25

<210> SEQ ID NO 39
<211> LENGTH: 26
<212> TYPE: DNA
<213> ORGANISM: artificial sequence
<220> FEATURE:
<223> OTHER INFORMATION: Artificial DNA primer

<400> SEQUENCE: 39
tagaggttgt ggttagggga agggtc                                 26

<210> SEQ ID NO 40
<211> LENGTH: 25
<212> TYPE: DNA
<213> ORGANISM: artificial sequence
<220> FEATURE:
<223> OTHER INFORMATION: Artificial DNA primer

<400> SEQUENCE: 40
aaatttacaa tcaattctac gcgct                                  25

<210> SEQ ID NO 41
<211> LENGTH: 32
<212> TYPE: DNA
<213> ORGANISM: artificial sequence
<220> FEATURE:
<223> OTHER INFORMATION: Artificial DNA primer

<400> SEQUENCE: 41
ttcgtagacg taattttttc gttttatagc gc                          32

<210> SEQ ID NO 42
<211> LENGTH: 25
<212> TYPE: DNA
<213> ORGANISM: artificial sequence
<220> FEATURE:

```
<223> OTHER INFORMATION: Artificial DNA primer

<400> SEQUENCE: 42
acttcctccg tcgaaatcgc taacg                                25

<210> SEQ ID NO 43
<211> LENGTH: 21
<212> TYPE: DNA
<213> ORGANISM: artificial sequence
<220> FEATURE:
<223> OTHER INFORMATION: Artificial DNA primer

<400> SEQUENCE: 43
cggttttcgt tcgtttttc g                                     21

<210> SEQ ID NO 44
<211> LENGTH: 18
<212> TYPE: DNA
<213> ORGANISM: artificial sequence
<220> FEATURE:
<223> OTHER INFORMATION: Artificial DNA primer

<400> SEQUENCE: 44
ccgccttcta cgcgacta                                        18
```

DETECTING CHOLANGIOCARCINOMA

CROSS-REFERENCE TO RELATED APPLICATIONS

This application is a continuation of U.S. patent application Ser. No. 16/242,695, filed Jan. 8, 2019, which is a continuation of U.S. patent application Ser. No. 14/864,158, filed Sep. 24, 2015, allowed as U.S. Pat. No. 10,184,154, which claims priority to U.S. Provisional Patent Application No. 62/055,737, filed Sep. 26, 2014, the contents of which are incorporated by reference in their entireties.

FIELD OF INVENTION

Provided herein is technology relating to detecting neoplasia and particularly, but not exclusively, to methods, compositions, and related uses for detecting neoplasms such as cholangiocarcinoma.

BACKGROUND

Cholangiocarcinomas (CCs) are malignancies of the biliary duct system that may originate in the liver and extrahepatic bile ducts, which terminate at the ampulla of Vater (see, e.g., Douglass H O, et al., In: Holland J F, et al, eds. Cancer Medicine. Vol 2. Philadelphia, Pa: Lea & Febiger. 1993:1455-62; Lake J R. B In: Sleisinger M H, Fordtran J S, eds. Gastrointestinal Disease. 5th ed. Vol 2. Philadelphia, Pa: WB Saunders. 1993:1891-1902; Lotze M T, et al., In: Devita V, Hellman S, Rosenberg S. *Cancer: Principles and Practice of Oncology.* 4th. Philadelphia, Pa: Lippincott; 1993: 883-907; de Groen P C, et al., *N Engl J Med. Oct.* 28 1999; 341(18):1368-78). CCs are encountered in 3 geographic regions: intrahepatic, extrahepatic (ie, perihilar), and distal extrahepatic. Perihilar tumors are the most common CCs, and intrahepatic tumors are the least common. Perihilar tumors, also called Klatskin tumors occur at the bifurcation of right and left hepatic ducts. Distal extrahepatic tumors are located from the upper border of the pancreas to the ampulla. More than 95% of these tumors are ductal adenocarcinomas; many patients present with unresectable or metastatic disease.

Cholangiocarcinoma is a tumor that arises from the intrahepatic or extrahepatic biliary epithelium. More than 90% are adenocarcinomas, and the remainder are squamous cell tumors. The etiology of most bile duct cancers remains undetermined. Long-standing inflammation, as with primary sclerosing cholangitis (PSC) or chronic parasitic infection, has been suggested to play a role by inducing hyperplasia, cellular proliferation, and, ultimately, malignant transformation. Intrahepatic cholangiocarcinoma may be associated with chronic ulcerative colitis and chronic cholecystitis.

Cholangiocarcinomas tend to grow slowly and to infiltrate the walls of the ducts, dissecting along tissue planes. Local extension occurs into the liver, porta hepatitis, and regional lymph nodes of the celiac and pancreaticoduodenal chains. Life-threatening infection (cholangitis) may occur that requires immediate antibiotic intervention and aggressive biliary drainage.

Despite aggressive anticancer therapy and interventional supportive care (ie, wall stents or percutaneous biliary drainage), median survival rate is low, since most patients (90%) are not eligible for curative resection. The overall survival is approximately 6 months.

As such, improved methods for early stage detection of cholangiocarcinomas is needed.

SUMMARY

Cholangiocarcinoma (CCA) is difficult to diagnose, even in high risk patients. Moreover, most patients who develop CCA do not have known risk factors. Imaging and cytology are specific but poorly sensitive. Because potentially curative treatments are available, there is critical need for complementary diagnostic and screening tools Provided herein is technology for CCA screening markers that provide a high signal-to-noise ratio and a low background level when detected from samples taken from a subject.

Markers and/or panels of markers (e.g., a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2) were identified in case-control studies by comparing the methylation state of DNA markers from intrahepatic and extrahepatic tissue samples from subjects with CCA to the methylation state of the same DNA markers from control subjects (see, Examples 1 and 2).

As described herein, the technology provides a number of methylated DNA markers and subsets thereof (e.g., sets of 2, 3, 4, 5, 6, 7, 8, 9, 10, 11, 12 or more markers) with high discrimination for CCA. Experiments applied a selection filter to candidate markers to identify markers that provide a high signal to noise ratio and a low background level to provide high specificity, e.g., when assaying distant media (e.g., stool, blood, urine, metastatic tissue, intra-hepatic tissue, extra-hepatic tissue, etc.) for purposes of cancer screening or diagnosis.

In some embodiments, the technology is related to assessing the presence of and methylation state of one or more of the markers identified herein in a biological sample. These markers comprise one or more differentially methylated regions (DMR) as discussed herein (see, Examples 1 and 2). Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) *Mol. Cell. Biol.* 14: 7421-7427) and another example involves methylation-sensitive arbitrarily primed PCR (Gonzalgo et al. (1997) *Cancer Res.* 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) *Nucl. Acids Res.* 18: 687). In addition, other techniques have been reported that utilize bisulfite treatment of DNA as a starting point for methylation analysis. These include methylation-specific PCR (MSP) (Herman et al. (1992) *Proc. Natl. Acad. Sci. USA* 93: 9821-9826) and restriction enzyme digestion of PCR products amplified from bisulfite-converted DNA (Sadri and Hornsby (1996) *Nucl. Acids Res.* 24: 5058-5059; and Xiong and Laird (1997) *Nucl. Acids Res.* 25: 2532-

2534). PCR techniques have been developed for detection of gene mutations (Kuppuswamy et al. (1991) *Proc. Natl. Acad. Sci. USA* 88: 1143-1147) and quantification of allelic-specific expression (Szabo and Mann (1995) *Genes Dev.* 9: 3097-3108; and Singer-Sam et al. (1992) *PCR Methods Appl.* 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106, incorporated herein by reference).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfate, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

Accordingly, provided herein is technology related to a method of screening for either intra-hepatic CCA or extra-hepatic CCA in a sample obtained from a subject, the method comprising assaying a methylation state of a marker in a sample obtained from a subject; and identifying the subject as having either intra-hepatic CCA or extra-hepatic CCA when the methylation state of the marker is different than a methylation state of the marker assayed in a subject that does not have a neoplasm (e.g., either intra-hepatic CCA or extra-hepatic CCA), wherein the marker comprises a chromosomal region having an annotation selected from HOXA1, EMX1, PRKCB, CYP26C1, LOC645323, ZNF781, ST8SIA1 and chr7.25896389-25896501 (see, Example 1). Some embodiments provide methods comprising assaying a plurality of markers, e.g., comprising assaying 2 to 8 markers.

Provided herein is technology related to a method of screening for intra-hepatic CCA in a sample obtained from a subject, the method comprising assaying a methylation state of a marker in a sample obtained from a subject; and identifying the subject as having intra-hepatic CCA when the methylation state of the marker is different than a methylation state of the marker assayed in a subject that does not have a neoplasm (e.g., intra-hepatic CCA), wherein the marker comprises a chromosomal region having an annotation selected from CYP26C1, EMX1, HIST1H1D, HOXA1, KLHDC7B, LBX2, LOC645323, chr5.77268600, chr6.28175437, chr7.25896389, PNMAL2, PRKCB, SP9, ST8SIA1, TRIM36, and ZNF781 (see, Example 1). Some embodiments provide methods comprising assaying a plurality of markers, e.g., comprising assaying 2 to 8 markers.

Provided herein is technology related to a method of screening for extra-hepatic CCA in a sample obtained from a subject, the method comprising assaying a methylation state of two markers in a sample obtained from a subject; and identifying the subject as having extra-hepatic CCA when the methylation state of the two markers are different than a methylation state of the marker assayed in a subject that does not have a neoplasm (e.g., extra-hepatic CCA), wherein the two marker comprises a chromosomal region having an annotation selected from CYP26C1 and LOC645323 (see, Example 1).

Provided herein is technology related to a method of screening for extra-hepatic CCA in a sample obtained from a subject, the method comprising assaying a methylation state of a marker in a sample obtained from a subject; and identifying the subject as having extra-hepatic CCA when the methylation state of the marker is different than a methylation state of the marker assayed in a subject that does not have a neoplasm (e.g., extra-hepatic CCA), wherein the marker comprises a chromosomal region having an annotation selected from EMX1, HOXA1, VSTM2B.764, KCNA1, BMP3, SALL1, PTGDR, and RYR2 (see, Example 2). Some embodiments provide methods comprising assaying a plurality of markers, e.g., comprising assaying 2 to 8 markers.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample, an intrahepatic tissue sample, a bile sample, duodenal fluid aspirate, an extrahepatic tissue sample, a blood sample (e.g., plasma, serum, whole blood), an excretion, or a urine sample. In some embodiments, the sample is obtained via a bile duct cytology brushing.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR. In some embodiments are provided an oligonucleotide comprising a sequence complementary to a chromosomal region having a base in a DMR, e.g., an oligonucleotide sensitive to methylation state of a DMR.

Kit embodiments are provided, e.g., a kit comprising a bisulfite reagent; and a control nucleic acid comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) and having a methylation state associated with a subject who does not have a cancer (e.g., intra-hepatic CCA or extra-hepatic CCA). In some embodiments, kits comprise a bisulfite reagent and an oligonucleotide as described herein. In some embodiments, kits comprise a bisulfite reagent; and a control nucleic acid comprising a sequence from such a chromosomal region and having a methylation state associated with a subject who has CCA (e.g., intra-hepatic CCA or extra-hepatic CCA). Some kit embodiments comprise a sample collector for obtaining a sample from a subject (e.g., a stool sample); reagents for isolating a nucleic acid from the sample; a bisulfite reagent; and an oligonucleotide as described herein.

The technology is related to embodiments of compositions (e.g., reaction mixtures). In some embodiments are provided a composition comprising a nucleic acid comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) and a bisulfite reagent. Some embodiments provide a composition comprising a nucleic acid comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) and an oligonucleotide as described herein. Some embodiments provide a composition comprising a nucleic acid comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) and a methylation-sensitive restriction enzyme. Some embodiments provide a composition comprising a nucleic acid comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) and a polymerase.

Additional related method embodiments are provided for screening for a neoplasm (e.g., intra-hepatic CCA or extra-hepatic CCA) in a sample obtained from a subject, e.g., a method comprising determining a methylation state of a marker in the sample comprising a base in a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2); comparing the methylation state of the marker from the subject sample to a methylation state of the marker from a normal control sample from a subject who does not have CCA (e.g., intra-hepatic CCA or extra-hepatic CCA); and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) with a bisulfite reagent to produce a bisulfite-reacted nucleic acid; sequencing the bisulfite-reacted nucleic acid to provide a nucleotide sequence of the bisulfite-reacted nucleic acid; comparing the nucleotide sequence of the bisulfite-reacted nucleic acid with a nucleotide sequence of a nucleic acid comprising the chromosomal region from a subject who does not have CCA (e.g., intra-hepatic CCA or extra-hepatic CCA) to identify differences in the two sequences; and identifying the subject as having a neoplasm when a difference is present.

Systems for screening for CCA (e.g., intra-hepatic CCA or extra-hepatic CCA) in a sample obtained from a subject are provided by the technology. Exemplary embodiments of systems include, e.g., a system for screening for CCA (e.g., intra-hepatic CCA or extra-hepatic CCA) in a sample obtained from a subject, the system comprising an analysis component configured to determine the methylation state of a sample, a software component configured to compare the methylation state of the sample with a control sample or a reference sample methylation state recorded in a database, and an alert component configured to alert a user of a cancer-associated methylation state. An alert is determined in some embodiments by a software component that receives the results from multiple assays (e.g., determining the methylation states of multiple markers, e.g., a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2)) and calculating a value or result to report based on the multiple results. Some embodiments provide a database of weighted parameters associated with each a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a CCA (e.g., intra-hepatic CCA or extra-hepatic CCA) risk in a subject.

In some embodiments of systems, a sample comprises a nucleic acid comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2). In some embodiments the system further comprises a component for isolating a nucleic acid, a component for collecting a sample such as a component for collecting a stool sample. In some embodiments, the system comprises nucleic acid sequences comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2). In some embodiments the database comprises nucleic acid sequences from subjects who do not have CCA. Also provided are nucleic acids, e.g., a set of nucleic acids, each nucleic acid having a sequence comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2). In some embodiments the set of nucleic acids wherein each nucleic acid has a sequence from a subject who does not have CCA. Related system embodiments comprise a set of nucleic acids as described and a database of nucleic acid sequences associated with the set of nucleic acids. Some embodiments further comprise a bisulfate reagent. And, some embodiments further comprise a nucleic acid sequencer.

In certain embodiments, methods for characterizing a sample obtained from a human subject are provided, comprising a) obtaining a sample from a human subject; b) assaying a methylation state of one or more markers in the sample, wherein the marker comprises a base in a chromosomal region having an annotation selected from the following groups of markers: HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2; and c) comparing the methylation state of the assayed marker to the methylation state of the marker assayed in a subject that does not have a neoplasm.

In some embodiments, the neoplasm is intra-hepatic cholangiocarcinoma or extra-hepatic cholangiocarcinoma.

In some embodiments, assaying the methylation state of the one or more markers in the sample comprises determining the methylation state of one or more bases for assayed marker.

In some embodiments, the methylation state of the one or more markers comprises an increased or decreased methylation of the assayed marker relative to a normal methylation state of the marker, and/or a different pattern of methylation of the assayed marker relative to a normal methylation state of the marker.

In some embodiments, the sample is a stool sample, a tissue sample, an intrahepatic tissue sample, an extrahepatic tissue sample, a blood sample, or a urine sample.

In some embodiments, the assaying comprises use of a methylation specific oligonucleotide selected from the group consisting of SEQ ID NO: 1-42.

Additional embodiments will be apparent to persons skilled in the relevant art based on the teachings contained herein.

DEFINITIONS

Figure 1:
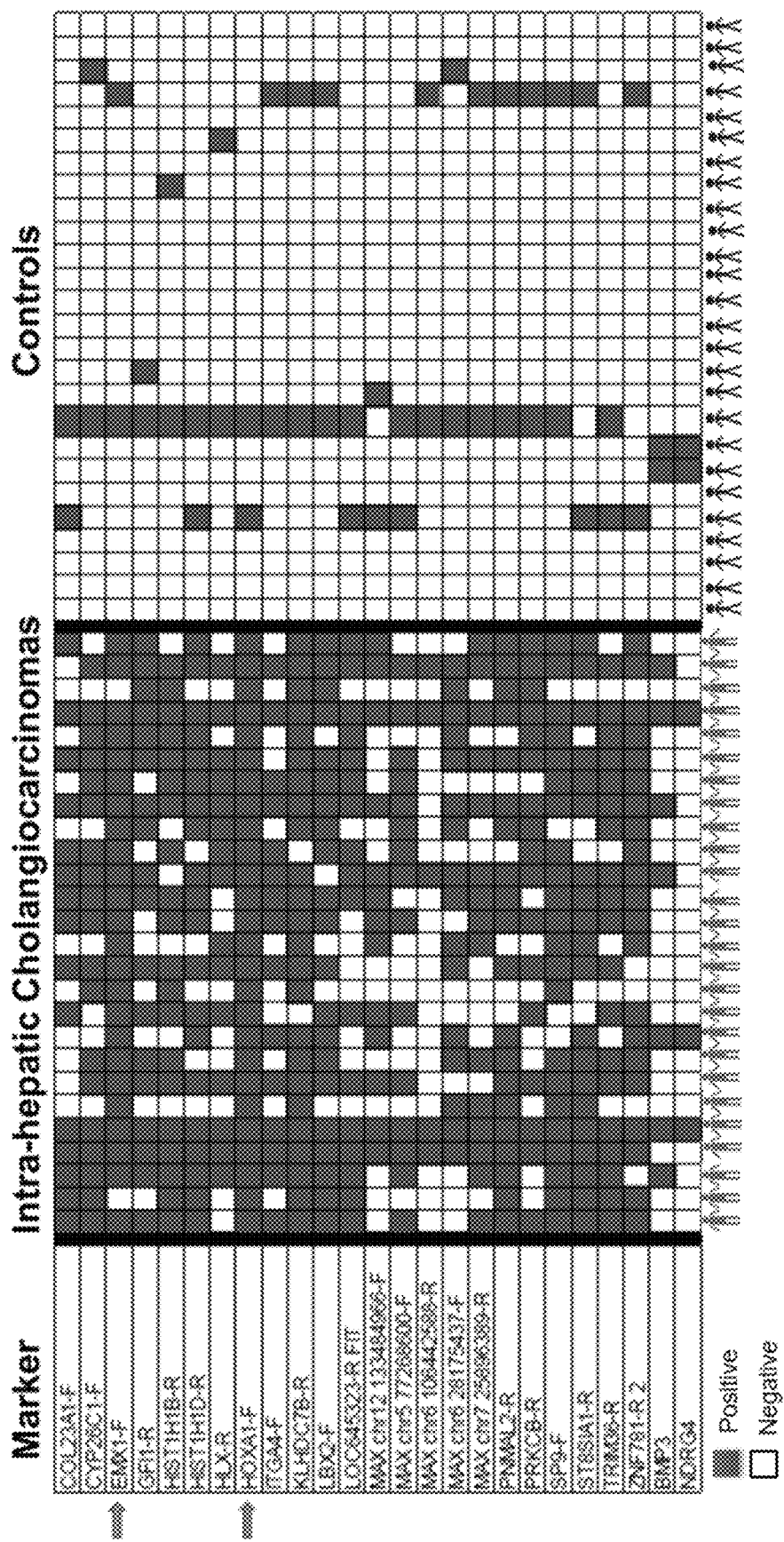
FIG. 1 shows the biological validation of candidate markers at 90% specificity for intra-hepatic cholangiocarcinomas (iCCAs). Notably, for iCCA, HOXA1 alone (AUC 0.99) yielded 100% sensitivity at 90% specificity.

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) *J. Mol. Biol.* 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) *Proc. Natl. Acad. Sci. USA* 97: 5237-5242; Salmon and Kaye (1970) *Biochim. Biophys. Acta.* 204: 340-351; Grafstrom (1985) *Nucleic Acids Res.* 13: 2827-2842; Nyce (1986) *Nucleic Acids Res.* 14: 4353-4367; Woodcock (1987) *Biochem. Biophys. Res. Commun.* 145: 888-894).

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) *Cancer Research* 57: 594-599.

The term "MethyLight™" refers to the art-recognized fluorescence-based real-time PCR technique described by Eads et al. (1999) *Cancer Res.* 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) *Nucleic Acids Res.* 25: 2529-2531.

The term "MSP" (Methylation-specific PCR) refers to the art-recognized methylation assay described by Herman et al. (1996) *Proc. Natl. Acad. Sci. USA* 93: 9821-9826, and by U.S. Pat. No. 5,786,146.

The term "COBRA" (Combined Bisulfite Restriction Analysis) refers to the art-recognized methylation assay described by Xiong & Laird (1997) *Nucleic Acids Res.* 25: 2532-2534.

The term "MCA" (Methylated CpG Island Amplification) refers to the methylation assay described by Toyota et al. (1999) *Cancer Res.* 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemimethylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) *Signal Detection Theory and ROC Analysis*, Academic Press, New York).

The term "marker", as used herein, refers to a substance (e.g., a nucleic acid or a region of a nucleic acid) that is able to diagnose a cancer by distinguishing cancerous cells from normal cells, e.g., based its methylation state.

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

DETAILED DESCRIPTION

Provided herein is technology relating to methods, compositions, and related uses for detecting CCA. As the technology is described herein, the section headings used are for organizational purposes only and are not to be construed as limiting the subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Provided herein is technology for cholangiocarcinoma (CCA) screening markers that provide a high signal-to-noise ratio and a low background level when detected from samples taken from a subject. Markers (e.g., a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2) were identified in a case-control study by comparing the methylation state of DNA markers from intrahepatic and extrahepatic tissue samples of subjects with CCA to the methylation state of the same DNA markers from control subjects (e.g., normal intrahepatic and/or extrahepatic tissue) (see, Examples 1 and 2).

In addition, the technology provides various panels of markers, e.g., in some embodiments the marker comprises a chromosomal region having an annotation that is HOXA1, EMX1, PRKCB, CYP26C1, LOC645323, ZNF781, ST8SIA1 and chr7.25896389-25896501, and that comprises the marker (see, Example 1).

In some embodiments the marker comprises a chromosomal region having an annotation that is CYP26C1, EMX1, HIST1H1D, HOXA1, KLHDC7B, LBX2, LOC645323, chr5.77268600, chr6.28175437, chr7.25896389, PNMAL2, PRKCB, SP9, ST8SIA1, TRIM36, and ZNF781, and that comprises the marker (see, Example 1).

In some embodiments the marker comprises a chromosomal region having an annotation that is CYP26C1 and LOC645323, and that comprises the marker (see, Example 1).

In some embodiments the marker comprises a chromosomal region having an annotation that is EMX1, HOXA1, VSTM2B.764, KCNA1, BMP3, SALL1, PTGDR, and RYR2, and that comprises the marker (see, Example 1).

Although the disclosure herein refers to certain illustrated embodiments, it is to be understood that these embodiments are presented by way of example and not by way of limitation.

In particular aspects, the present technology provides compositions and methods for identifying, determining, and/or classifying CCA. The methods comprise determining the methylation status of at least one methylation marker in a biological sample isolated from a subject, wherein a change in the methylation state of the marker is indicative of the presence, class, or site of CCA. Particular embodiments relate to markers comprising a differentially methylated region (a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2)) that are used for diagnosis (e.g., screening) of CCA (e.g., intra-hepatic CCA or extra-hepatic CCA).

In addition to embodiments wherein the methylation analysis of at least one marker, a region of a marker, or a base of a marker comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) provided herein is analyzed, the technology also provides panels of such markers with utility for the detection of CCA (e.g., intra-hepatic CCA or extra-hepatic CCA).

Some embodiments of the technology are based upon the analysis of the CpG methylation status of at least one marker, region of a marker, or base of a marker comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2).

In some embodiments, the present technology provides for the use of the bisulfite technique in combination with one or more methylation assays to determine the methylation status of CpG dinucleotide sequences within at least one marker comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) has utility both in the diagnosis and characterization of CCA (e.g., intra-hepatic CCA or extra-hepatic CCA).

Methods for Assaying Methylation State

The most frequently used method for analyzing a nucleic acid for the presence of 5-methylcytosine is based upon the bisulfite method described by Frommer, et al. for the detection of 5-methylcytosines in DNA (Frommer et al. (1992) *Proc. Natl. Acad. Sci. USA* 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uricil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98) or methylation-specific PCR (MSP) as is disclosed, e.g., in U.S. Pat. No. 5,786,146.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" *Nucleic Acids Res.* 24: 5064-6). It is thus possible to analyze individual cells for methylation status, illustrating the utility and sensitivity of the method. An overview of conventional methods for detecting 5-methylcytosine is provided by Rein, T., et al. (1998) *Nucleic Acids Res.* 26: 2255.

The bisulfite technique typically involves amplifying short, specific fragments of a known nucleic acid subsequent to a bisulfite treatment, then either assaying the product by sequencing (Olek & Walter (1997) *Nat. Genet.* 17: 275-6) or a primer extension reaction (Gonzalgo & Jones (1997)

Nucleic Acids Res. 25: 2529-31; WO 95/00669; U.S. Pat. No. 6,251,594) to analyze individual cytosine positions. Some methods use enzymatic digestion (Xiong & Laird (1997) Nucleic Acids Res. 25: 2532-4). Detection by hybridization has also been described in the art (Olek et al., WO 99/28498). Additionally, use of the bisulfite technique for methylation detection with respect to individual genes has been described (Grigg & Clark (1994) Bioessays 16: 431-6; Zeschnigk et al. (1997) Hum Mol Genet. 6: 387-95; Feil et al. (1994) Nucleic Acids Res. 22: 695; Martin et al. (1995) Gene 157: 261-4; WO 9746705; WO 9515373).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) Proc. Natl. Acad. Sci. USA 89: 1827-1831). Additionally, restriction enzyme digestion of PCR products amplified from bisulfite-converted DNA finds use in assessing methylation state, e.g., as described by Sadri & Hornsby (1997) Nucl. Acids Res. 24: 5058-5059 or as embodied in the method known as COBRA (Combined Bisulfite Restriction Analysis) (Xiong & Laird (1997) Nucleic Acids Res. 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can by used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, DMR, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" *Nat Methods* 7: 133-6; Meissner et al. (2005) "Reduced representation bisulfite sequencing for comparative high-resolution DNA methylation analysis" *Nucleic Acids Res.* 33: 5868-77.

In some embodiments, a quantitative allele-specific real-time target and signal amplification (QUARTS) assay is used to evaluate methylation state. Three reactions sequentially occur in each QUARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes cleavase to release the flap sequence by cutting between the detection probe and the flap sequence. The flap sequence is complementary to a nonhairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" *Clin Chem* 56: A199; U.S. Pat. No. 8,361,720; U.S. patent application Ser. No. 12/946,745, U.S. Pat. No. 8,715,937, and Ser. No. 13/594,674.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715, which is incorporated by reference in its entirety). It is preferred that the bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). The bisulfite conversion is preferably carried out at a reaction temperature between 30° C. and 70° C., whereby the temperature is increased to over 85° C. for short times during the reaction (see: PCT/EP2004/011715, which is incorporated by reference in its entirety). The bisulfite treated DNA is preferably purified prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715, which is incorporated by reference in its entirety).

In some embodiments, fragments of the treated DNA are amplified using sets of primer oligonucleotides according to the present invention and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids"), incorporated herein by reference in its entirety.

Methods

In some embodiments the technology, methods are provided that comprise the following steps:
a) obtaining a sample from a human subject;
b) assaying a methylation state of one or more markers in the sample, wherein the marker comprises a base in a chromosomal region having an annotation selected from the following groups of markers: HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2;
c) comparing the methylation state of the assayed marker to the methylation state of the marker assayed in a subject that does not have a neoplasm.

In some embodiments the technology, methods are provided that comprise the following steps:
1) assaying a methylation state of a marker in a sample obtained from a subject, wherein the marker comprises a base in a chromosomal region having an annotation selected from the following groups of markers: HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2; and 2) identifying the subject as having a neoplasm when the methylation state of the marker is different than a methylation state of the marker assayed in a subject that does not have a neoplasm (e.g., afforded with a sensitivity of greater than or equal to 80% and a specificity of greater than or equal to 80%).

Preferably, the sensitivity is from about 70% to about 100%, or from about 80% to about 90%, or from about 80% to about 85%. Preferably, the specificity is from about 70% to about 100%, or from about 80% to about 90%, or from about 80% to about 85%.

In some embodiments, the neoplasm is:
- either intra-hepatic cholangiocarcinoma or extra-hepatic cholangiocarcinoma if the methylation state of one or more of the following markers is different than a methylation state of the respective marker assayed in a subject that does not have either intra-hepatic cholangiocarcinoma or extra-hepatic cholangiocarcinoma: HOXA1, EMX1, PRKCB, CYP26C1, LOC645323, ZNF781, ST8SIA1 and chr7.25896389-25896501;
- intra-hepatic cholangiocarcinoma if the methylation state of one or more of the following markers is different than a methylation state of the respective marker assayed in a subject that does not have intra-hepatic cholangiocarcinoma: CYP26C1, EMX1, HIST1H1D, HOXA1, KLHDC7B, LBX2, LOC645323, chr5.77268600, chr6.28175437, chr7.25896389, PNMAL2, PRKCB, SP9, ST8SIA1, TRIM36, and ZNF781;
- extra-hepatic cholangiocarcinoma if the methylation state of the following markers is different than a methylation state of the respective marker assayed in a subject that does not have extra-hepatic cholangiocarcinoma: CYP26C1 and LOC645323; and/or
- extra-hepatic cholangiocarcinoma if the methylation state of one or more of the following markers is different than a methylation state of the respective marker assayed in a subject that does not have extra-hepatic cholangiocarcinoma: EMX1, HOXA1, VSTM2B.764, KCNA1, BMP3, SALL1, PTGDR, and RYR2.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, colonic effluent, urine, blood plasma, blood serum, whole blood, isolated blood cells, cells isolated from the blood, and combinations thereof. In some embodiments, the clinical sample type is intra-hepatic CCA tissue or extra-hepatic CCA tissue.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfate (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2). The method of analysis may be selected from those known in the art, including those listed herein, e.g., QUARTS and MSP as described herein.

Aberrant methylation, more specifically hypermethylation of a marker comprising a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) is associated with CCA.

The technology relates to the analysis of any sample associated with CCA. For example, in some embodiments the sample comprises a tissue and/or biological fluid obtained from a patient. In some embodiments, the sample comprises a secretion. In some embodiments, the sample comprises blood, serum, plasma, gastric secretions, intrahepatic tissue samples, extrahepatic tissue samples, a gastrointestinal biopsy sample, microdissected cells from a gastrointestinal biopsy, gastrointestinal cells sloughed into the gastrointestinal lumen, and/or gastrointestinal cells recovered from stool. In some embodiments, the subject is human. These samples may originate from the upper gastrointestinal tract, the lower gastrointestinal tract, or comprise cells, tissues, and/or secretions from both the upper gastrointestinal tract and the lower gastrointestinal tract. The sample may include cells, secretions, or tissues from the liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample. In some embodiments, the sample is intra-hepatic CCA tissue or extra-hepatic CCA tissue.

Such samples can be obtained by any number of means known in the art, such as will be apparent to the skilled person. For instance, urine and fecal samples are easily attainable, while blood, ascites, serum, or fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens In some embodiments, the technology relates to a method for treating a patient (e.g., a patient with CCA), the method comprising determining the methylation state of one or more chromosomal regions having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing CCA in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2)), the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2)) disclosed herein. Further, in some embodiments of the presently disclosed subject matter, multiple determination of the biomarkers over time can be made to facilitate diagnosis and/or prognosis. A temporal change in the biomarker can be used to predict a clinical outcome, monitor the progression of cholangiocarcinoma, and/or monitor the efficacy of appropriate therapies directed against the cancer. In such an embodiment for example, one might expect to see a change in the methylation state of one or more biomarkers (e.g., a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2)) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with risk for developing cholangiocarcinoma, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2)). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more chromosomal regions having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2)), the chance of a given outcome (e.g., suffering from CCA) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2)) can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with cholangiocarcinoma. In certain embodiments of the method, a subject is identified as having metaplasia upon identifying an aberrant methylation state of one or more chromosomal regions having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2) provided herein in a biological sample obtained from the subject. In other embodiments of the method, the detection of an aberrant methylation state of one or more of such biomarkers in a biological sample obtained from the subject results in the subject being identified as having cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having cholangiocarcinoma if, when compared to a control methylation state, there is a measurable difference in the methylation state of at least one biomarker in the sample. Conversely, when no change in methylation state is identified in the biological sample, the subject can be identified as not having cholangiocarcinoma, not being at risk for the cancer, or as having a low risk of the cancer. In this regard, subjects having cholangiocarcinoma or risk thereof can be differentiated from subjects having low to substantially no cancer or risk thereof. Those subjects having a risk of developing cholangiocarcinoma can be placed on a more intensive and/or regular screening schedule, including endoscopic surveillance. On the other hand, those subjects having low to substantially no risk may avoid being subjected to a screening procedure, until such time as a future screening, for example, a screening conducted in accordance with the present technology, indicates that a risk of CCA has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, cholangiocarcinoma indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like. The presently-disclosed subject matter further includes a system for diagnosing CCA in a subject. The system can be provided, for example, as a commercial kit that can be used to screen for a risk of CCA or diagnose CCA in a subject from whom a biological sample has been collected. An exemplary system provided in accordance with the present technology includes assessing the methylation state of a chromosomal region having an annotation selected from HOXA1, EMX1, PRKCB, CYP26C1, LOC645323, ZNF781, ST8SIA1, chr7.25896389-25896501, VSTM2B.764, KCNA1, BMP3, SALL1, PTGDR, HIST1H1D, KLHDC7B, LBX2, chr5.77268600, chr6.28175437, PNMAL2, SP9, TRIM36, and RYR2 (see, Examples 1 and 2).

EXAMPLES

Example 1

Cholangiocarcinoma (CCA) prognosis is poor owing to late-stage, symptomatic presentation. New screening technologies are needed. Experiments conducted during the course of developing embodiments for the present invention used methylome-wide sequencing for discovery of highly discriminant methylated DNA markers for CCA with confirmation in independent samples.

Methods: Reduced representation bisulfate sequencing (RRBS) was performed to identify differentially hypermethylated CpG regions on DNA extracted from 17 frozen intrahepatic CCA (iCCA) tissue samples in comparison to matched, adjacent benign bile duct epithelia. Sequenced reads were mapped to a bisulfate-treated in-silico reference genome and annotated. CpGs with average group coverage of <200 reads were not further considered. Variance-inflated logistic regression estimated the strength of association between methylation-% and iCCA. Significant sites were then parsed into continuous differentially methylated regions (DMR) containing at least 3 CpGs. DMRs were selected for validation testing based on high discrimination, measured by area under the receiver operating characteristics curve (AUC), and signal to noise ratio. Top novel markers were then blindly assayed by methylation specific PCR on DNA extracted from an independent frozen tissue archive of iCCA (n=27), extrahepatic CCA (eCCA) (n=24) and matched, benign control samples for each.

Results: RRBS discovery mapped ~5-6 million CpGs. After filtration criteria, these clustered into 183 significant DMRs, each containing 6-103 CpGs. Among the 23 markers selected for validation testing, 16 showed an AUC of 0.80-1.0 in iCCA (e.g., CYP26C1, EMX1, HIST1H1D, HOXA1, KLHDC7B, LBX2, LOC645323, chr5.77268600, chr6.28175437, chr7.25896389, PNMAL2, PRKCB, SP9, ST8SIA1, TRIM36, and ZNF781). While selected marker candidates were slightly less accurate for eCCA, 8 proved highly discriminant for tumors in both anatomic locations. HOXA1, EMX1, PRKCB, CYP26C1, LOC645323, ZNF781, ST8SIA1 and chr7.25896389-25896501 showed AUCs of 0.99, 0.96, 0.93, 0.92, 0.90, 0.87, 0.85 & 0.84 and 0.84, 0.89, 0.81, 0.86, 0.86, 0.81, 0.80 & 0.83 for iCCA and eCCA, respectively. Multiple marker combinations improved sensitivity for eCCA. The most discriminant marker pair was CYP26C1 and LOC645323, which exhibited sensitivity of 83% for eCCA at a specificity of 95% (AUC 0.92).

Table 1 shows discriminate cholangiocarcinoma markers including forward and reverse primers for CYP26C1, EMX1, HOXA1, KLHDC7B, LOC645323, chr7.25896389, PRKCB, SP9, ST8SIA1, and ZNF781 (and additionally BMP3, NDRG4, HIST1H1D, LBX2, chr5.7726860, chr.6.2817543, PNMAL2, and TRIM36).

Tables 2 and 3 show two sets of differentially methylated regions for the detection of intra and extra-hepatic cholangiocarcinoma. The first set (Table 2) contains 91 DMRs and was generated from 18 microdissected frozen intrahepatic cholangiocarcinoma tissues using both normal colonic and normal pancreas as controls. The second set (Table 3) contains 90 DMRs and used normal pancreas tissue as control. The former set will find application generally in stool or other assays where normal colonic contamination could occur, and the latter to all other media, including pancreatic juice, blood, tissue, etc. Subsequent MSP-based technical and biological validations of 23 top candidates were performed. RRBS was used to query the entire methylomes of sample cohorts. Sequencing reads were analyzed using internally developed algorithms and filters designed to yield highly sensitive and specific DMRs. These DMRs were then used to design methylation-specific PCR assays using the most discriminate CpG patterns. Performance characteristics in tissues yield AUCs in excess of 0.85 and fold change ratios greater than 20. 9 of the cholangiocarcinoma MSP assays were used in a recent GI-wide study to assess site-specificity. The HOXA1 assay, in particular, was positive for pancreatic and biliary cancers and much less so for other GI cancers.

FIG. 1 shows the biological validation of candidate markers at 90% specificity for intra-hepatic cholangiocarcinomas (iCCAs). Notably, for iCCA, HOXA1 alone (AUC 0.99) yielded 100% sensitivity at 90% specificity.

Figure 2:
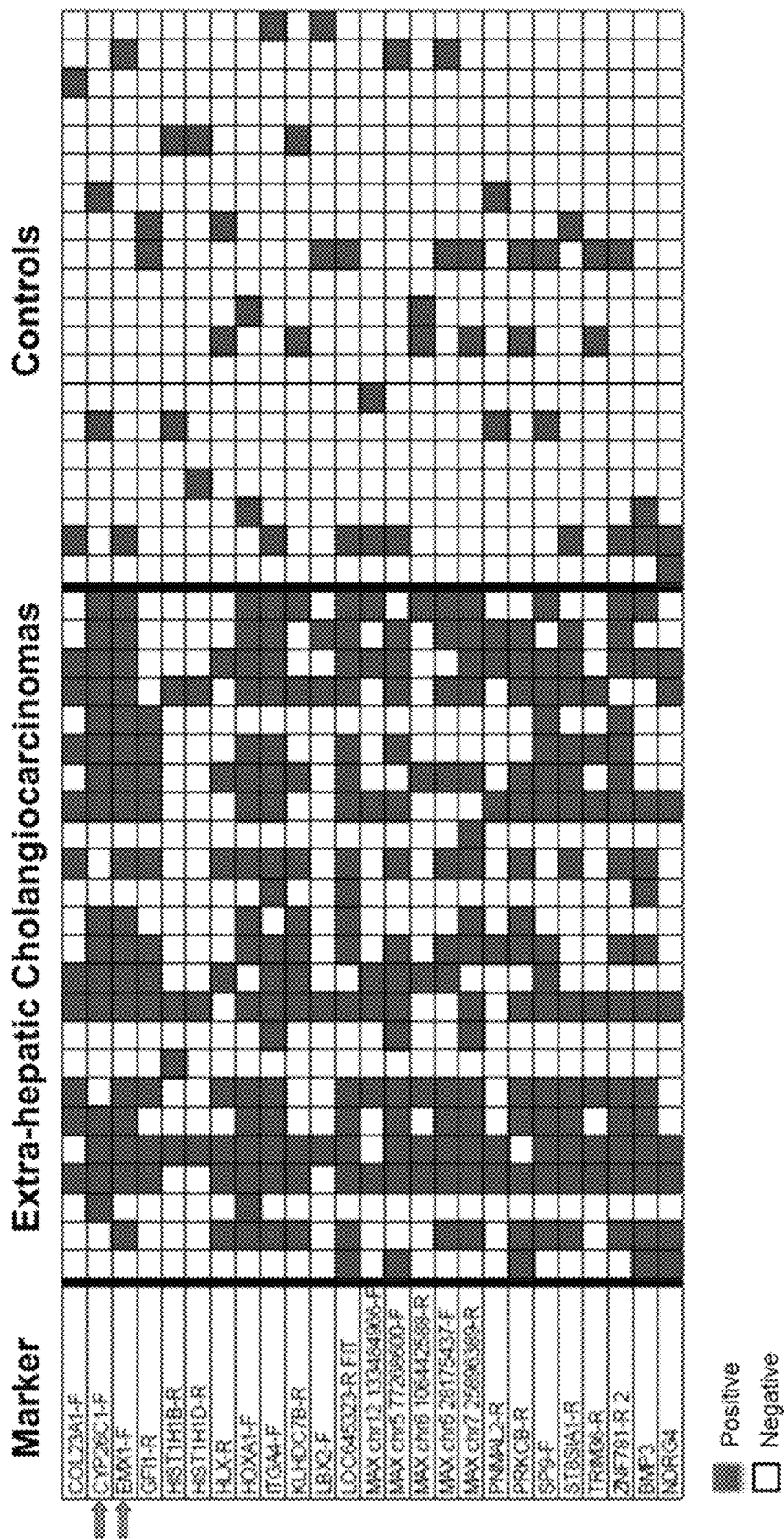
FIG. 2 shows the biological validation of candidate markers at 90% specificity for extra-hepatic cholangiocarcinomas (eCCAs). Notably, for eCCA, the marker pair CYP26C1 and LOC645323 (AUC 0.92) was 83% sensitive at 90% specificity.

FIG. 2 shows the biological validation of candidate markers at 90% specificity for extra-hepatic cholangiocarcinomas (eCCAs). Notably, for eCCA, the marker pair CYP26C1 and LOC645323 (AUC 0.92) was 83% sensitive at 90% specificity.

Figure 3:
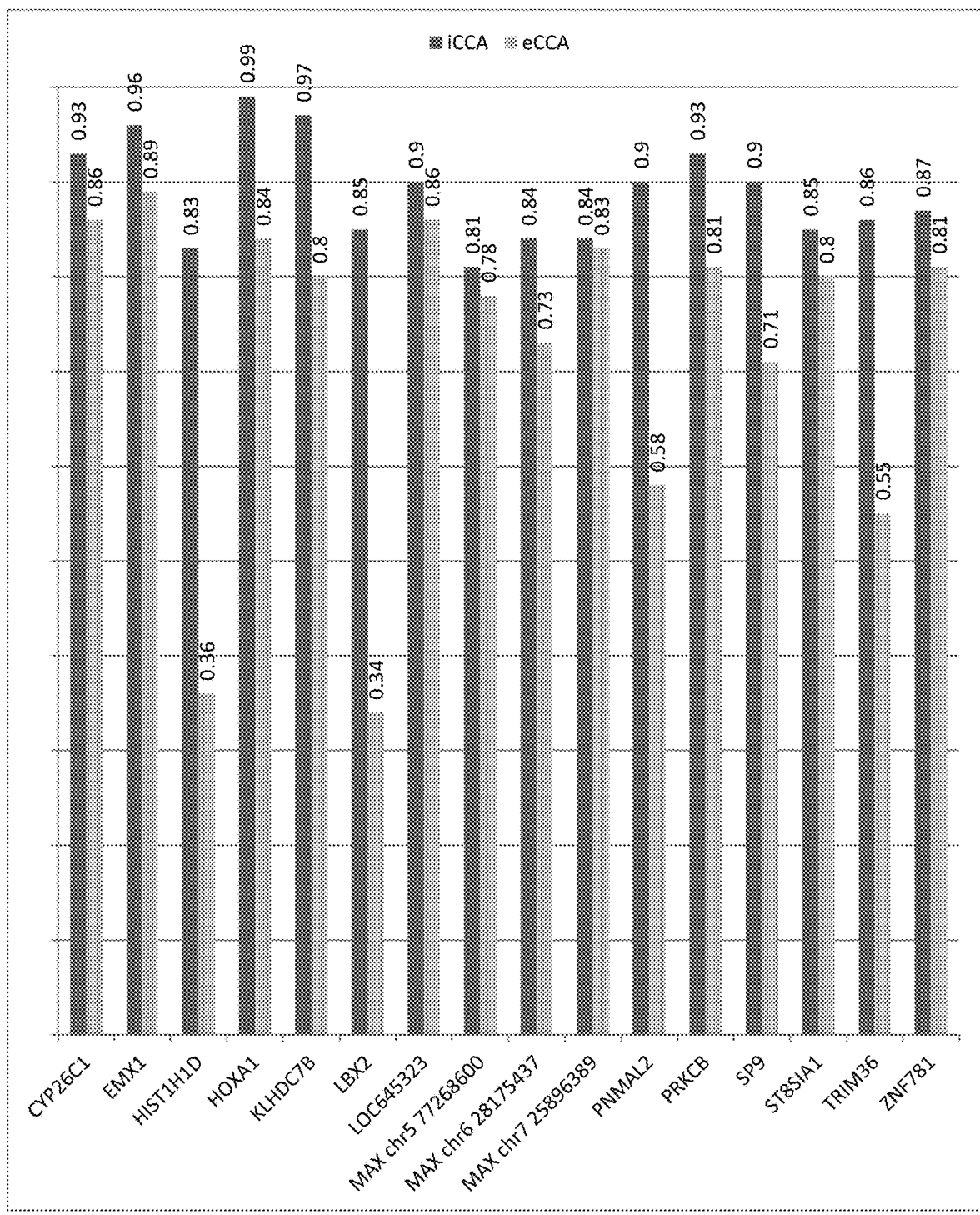
FIG. 3 shows AUC for iCCA and eCCA for the 16 markers among the 23 markers selected for validation testing. The first column for each marker is for iCCA. The second column for each marker is for eCCA.

FIG. 3 shows AUC for iCCA and eCCA for the 16 markers among the 23 markers selected for validation testing. The first column for each marker is for iCCA. The second column for each marker is for eCCA.

Conclusion: Novel methylation markers for CCA were identified by RRBS and validated in both iCCA and eCCA.

TABLE 1

Discriminate Cholangiocarcinoma Markers

| Marker | AUC | Forward Primer | Reverse Primer |
|---|---|---|---|
| BMP3 | 0.72926892 | GTTTAATTTTCG GTTTCGTCGTC (SEQ ID NO: 25) | CGCTACGAAACA CTCCGA (SEQ ID NO: 26) |
| NDRG4 | 0.63484888 | CGGTTTTCGTTC GTTTTTTCG (SEQ ID NO: 43) | CCGCCTTCTACG CGACTA (SEQ ID NO: 44) |
| COL23A1 | 0.7000775 | | |
| CYP26C1 | 0.92301731 | GGT TTT TTG GTT ATT TCG GAA TCG T (SEQ ID NO: 1) | TAT AAA AAC GCG CGT AAT CAA CGC T (SEQ ID NO: 2) |
| EMX1 | 0.94420047 | CGG GTT TTA GCG ATG TTT ATT TTA GTT TCG T (SEQ ID NO: 3) | CCT TTT CGT TCG TAT AAA ATT TCG TT (SEQ ID NO: 4) |
| GFI1 | 0.8276931 | | |
| HIST1H1B | 0.63291139 | | |
| HIST1H1D | 0.75716869 | GGC GTA ATT GTT GGG AAA CGT AAA GTA TTC (SEQ ID NO: 33) | GAC CAA AAA AAC GCC GCT ACG CT (SEQ ID NO: 34) |
| HLX | 0.77305606 | | |
| HOXA1 | 0.94833376 | TGG GTT ATC GGT TTT TTA AGT TCG G (SEQ ID NO: 5) | GAA TTC CTC CCA ACC AAC CCT CTA CG (SEQ ID NO: 6) |
| ITGA4 | 0.83027641 | | |
| KLHDC7B | 0.89899251 | TAG TAC GTT TAG GTA ATT GTT TAG GTT TAG TCG T (SEQ ID NO: 7) | CGA AAA CCC AAC TCC CGA A (SEQ ID NO: 8) |
| LBX2 | 0.69000258 | CGT CGC GGA ATT TAG GGA TTA ACG (SEQ ID NO: 35) | ATA CCA AAA CTC GCA CCT ACG AC (SEQ ID NO: 36) |
| LOC645323 | 0.87910101 | GGT AGT GTT TTT TCG AGA CGC GGTC (SEQ ID NO: 9) | GAT ACG CGA ACA CGC ACA CG (SEQ ID NO: 10) |
| LOC645323.R | 0.77344356 | | |
| chr12.133484966.133485778 | 0.68612762 | | |
| chr5.77268600.77268725 | 0.79101008 | TAT TTT ATA GTC GCG TTA AAA GCGT (SEQ ID NO: 37) | GTC GAT AAA AAA CCT ACG CGA CGA A (SEQ ID NO: 38) |
| chr6.106442588.106443096 | 0.71557737 | | |
| chr6.28175467.28175596 | 0.84603462 | TAG AGG TTG TGG TTA GGG GAA GGG TC (SEQ ID NO: 39) | AAA TTT ACA ATC AAT TCT ACG CGC T (SEQ ID NO: 40) |
| chr7.25896389.25896501 | 0.91010075 | GTT TTT CGT TGA GTT AGA AGC GTT (SEQ ID NO: 11) | ACC TCA ATA TAA ATA AAA ACG CAA (SEQ ID NO: 12) |

TABLE 1-continued

Discriminate Cholangiocarcinoma Markers

| Marker | AUC | Forward Primer | Reverse Primer |
|---|---|---|---|
| PNMAL2 | 0.82640145 | TTC GTA GAC GTA ATT TTT TCG TTT TAT AGC GC (SEQ ID NO: 41) | ACT TCC TCC GTC GAA ATC GCT AAC G (SEQ ID NO: 42) |
| PRKCB | 0.90260915 | GTC GTT TTT GGG CGT TTT AGA GGC (SEQ ID NO: 13) | TAA TCC CAA ACG AAC CGC CG (SEQ ID NO: 14) |
| SP9 | 0.87367605 | CGG GGG TAA AAA GGG TAG CGA TAG TGA TAC (SEQ ID NO: 15) | CGA AAA ATT CGA AAC GAA ACG TC (SEQ ID NO: 16) |
| ST8SIA1 | 0.85326789 | CGG TTG TTT AAC GAG AAA GAG ATC GT (SEQ ID NO: 17) | GAT CTA ATT CCT CCT CCA CGC CGT A (SEQ ID NO: 18) |
| TRIM36 | 0.78093516 | TTT GTC GGT ATG CGA TAA AGG TCG G (SEQ ID NO: 33) | ACG AAT CCG CAC TCG ACT CAA CG (SEQ ID NO: 34) |
| ZNF781 | 0.83143891 | CGC GGT GAG TTT AGT TAT TGA TTT TTA ACG G (SEQ ID NO: 19) | AAC GTC CAA AAC GCC CAA ACG TA (SEQ ID NO: 20) |

TABLE 2

Cholangiocarcinoma DMRs generated from 18 microdissected frozen intrahepatic cholangiocarcinoma tissues using both normal colonic and normal pancreas as controls

| Chromosome | Chromosome Coordinates | Gene Annotation |
|---|---|---|
| chr18 | 21199475-21199636 | ANKRD29 |
| chr12 | 21680721-21680828 | C12orf39 |
| chr12 | 2800272-2800464 | CACNA1C |
| chr12 | 2162474-2162746 | CACNA1C |
| chr17 | 48639261-48639451 | CACNA1G |
| chr16 | 89008467-89008548 | CBFA2T3 |
| chr16 | 89007265-89007360 | CBFA2T3 |
| chr3 | 112052188-112052342 | CD200 |
| chr3 | 142839223-142839495 | CHST2 |
| chr3 | 142838025-142838494 | CHST2 |
| chr5 | 178017215-178017456 | COL23A1 |
| chr10 | 94822416-94822607 | CYP26C1 |
| chr12 | 49391148-49391271 | DDN |
| chr11 | 118663134-118663291 | DDX6 |
| chr7 | 102921398-102921511 | DPY19L2P2 |
| chr2 | 73147710-73147772 | EMX1 |
| chr19 | 55592007-55592125 | EPS8L1 |
| chr19 | 55592819-55592937 | EPS8L1 |
| chr19 | 55591690-55591753 | EPS8L1 |
| chr13 | 28674551-28674643 | FLT3 |
| chr16 | 86542943-86543036 | FOXF1 |
| chr2 | 20866066-20866336 | GDF7 |

TABLE 2-continued

Cholangiocarcinoma DMRs generated from 18 microdissected frozen intrahepatic cholangiocarcinoma tissues using both normal colonic and normal pancreas as controls

| Chromosome | Chromosome Coordinates | Gene Annotation |
|---|---|---|
| chr1 | 92948946-92949053 | GFI1 |
| chr1 | 235813658-235813798 | GNG4 |
| chr7 | 6570511-6570865 | GRID2IP |
| chr6 | 27834959-27835386 | HIST1H1B |
| chr6 | 26234861-26235051 | HIST1H1D |
| chr6 | 26273744-26273792 | HIST1H3G |
| chr1 | 221052351-221052479 | HLX |
| chr1 | 221053381-221053616 | HLX |
| chr10 | 124895270-124895437 | HMX3 |
| chr7 | 27136145-27136425 | HOXA1 |
| chr7 | 27135603-27136002 | HOXA1 |
| chr7 | 27209650-27209687 | HOXA9 |
| chr17 | 46655791-46655837 | HOXB3 |
| chr17 | 46688289-46688399 | HOXB7 |
| chr17 | 46690336-46690596 | HOXB7 |
| chr17 | 47073401-47073437 | IGF2BP1 |
| chr7 | 23508914-23509225 | IGF2BP3 |
| chr20 | 20348855-20348967 | INSM1 |
| chr20 | 20348213-20348415 | INSM1 |
| chr2 | 182322268-182322409 | ITGA4 |
| chr2 | 182321848-182321983 | ITGA4 |
| chr16 | 87636217-87636415 | JPH3 |
| chr12 | 4919001-4919087 | KCNA6 |
| chr22 | 50987205-50987270 | KLHDC7B |
| chr2 | 74726179-74726257 | LBX2 |
| chr8 | 72756221-72756295 | LOC100132891 |
| chr4 | 13549245-13549293 | LOC285548 |
| chr5 | 87970706-87970894 | LOC645323 |
| chr15 | 84748863-84748932 | LOC648809 |
| chr11 | 61276632-61276910 | LRRC1OB |
| chr19 | 3786252-3786371 | MATK |
| chr1 | 156405616-156405739 | MAX.chr1.156405616-156405739 |
| chr1 | 32237942-32238004 | MAX.chr1.32237942-32238004 |
| chr10 | 119312919-119312997 | MAX.chr10.119312919-119312997 |
| chr11 | 123301058-123301255 | MAX.chr11.123301058-123301255 |
| chr12 | 133484966-133485778 | MAX.chr12.133484966-133485778 |
| chr2 | 105488742-105489008 | MAX.chr2.105488742-105489008 |
| chr2 | 118981853-118981949 | MAX.chr2.118981853-118981949 |
| chr20 | 3229317-3229692 | MAX.chr20.3229317-3229692 |
| chr22 | 42679617-42680017 | MAX.chr22.42679617-42680017 |
| chr4 | 113445045-113445162 | MAX.chr4.113445045-113445162 |
| chr5 | 10333495-10333893 | MAX.chr5.10333495-10333893 |
| chr5 | 134879359-134879492 | MAX.chr5.134879359-134879492 |
| chr5 | 42995283-42995370 | MAX.chr5.42995283-42995370 |
| chr6 | 106442588-106443096 | MAX.chr6.106442588-106443096 |
| chr6 | 26234019-26234186 | MAX.chr6.26234019-26234186 |
| chr6 | 91320565-91320758 | MAX.chr6.91320565-91320758 |
| chr7 | 25896389-25896501 | MAX.chr7.25896389-25896501 |
| chr7 | 99595323-99595474 | MAX.chr7.99595323-99595474 |
| chr9 | 114074-114367 | MAX.chr9.114074-114367 |
| chr9 | 79627079-79627175 | MAX.chr9.79627079-79627175 |
| chr6 | 108490524-108490539 | NR2E1 |

TABLE 2-continued

Cholangiocarcinoma DMRs generated from 18 microdissected frozen intrahepatic cholangiocarcinoma tissues using both normal colonic and normal pancreas as controls

| Chromosome | Chromosome Coordinates | Gene Annotation |
|---|---|---|
| chr5 | 139283409-139283483 | NRG2 |
| chr12 | 5541234-5541271 | NTF3 |
| chr8 | 99957451-99957607 | OSR2 |
| chr12 | 94543138-94543232 | PLXNC1 |
| chr19 | 46996606-46996841 | PNMAL2 |
| chr16 | 23847825-23848025 | PRKCB |
| chr16 | 23847575-23847621 | PRKCB |
| chr4 | 42399341-42399431 | SHISA3 |
| chr2 | 175202025-175202158 | SP9 |
| chr12 | 22486861-22487019 | ST8SIA1 |
| chr12 | 22487528-22487620 | ST8SIA1 |
| chr10 | 17496572-17496711 | ST8SIA6 |
| chr7 | 100224376-100224475 | TFR2 |
| chr5 | 114516047-114516319 | TRIM36 |
| chr6 | 3230007-3230059 | TUBB2B |
| chr6 | 150260025-150260157 | ULBP2 |
| chr19 | 38182950-38183127 | ZNF781 |

TABLE 3

Cholangiocarcinoma DMRs using normal pancreas as controls

| Chromosome | Chromosome Coordinates | Gene Annotation |
|---|---|---|
| chr1 | 145562791-145562906 | ANKRD35 |
| chr12 | 21680381-21680442 | C12orf39 |
| chr8 | 69243423-69243884 | C8orf34 |
| chr12 | 2162474-2162804 | CACNA1C |
| chr3 | 112052188-112052405 | CD200 |
| chr5 | 115152371-115152505 | CDO1 |
| chr7 | 136555719-136556019 | CHRM2 |
| chr12 | 111472738-111472835 | CUX2 |
| chr10 | 94834019-94834583 | CYP26A1 |
| chr21 | 27945125-27945267 | CYYR1 |
| chr13 | 50701723-50701817 | DLEU2 |
| chr18 | 67068438-67068578 | DOK6 |
| chr18 | 2847538-2847945 | EMILIN2 |
| chr18 | 5543753-5543932 | EPB41L3 |
| chr19 | 55592819-55592937 | EPS8L1 |
| chr7 | 27278981-27279087 | EVX1 |
| chr13 | 29068322-29068446 | FLT1 |
| chr10 | 26504030-26504426 | GAD2 |
| chr18 | 74961713-74962090 | GALR1 |
| chr3 | 128212076-128212146 | GATA2 |
| chr2 | 20866066-20866336 | GDF7 |
| chr12 | 129338638-129338792 | GLT1D1 |
| chr1 | 101005457-101005685 | GPR88 |
| chr1 | 101004620-101005237 | GPR88 |
| chr6 | 26273744-26273884 | HIST1H3G |
| chr1 | 221052023-221052602 | HLX |
| chr1 | 221053381-221053842 | HLX |
| chr4 | 57522513-57522653 | HOPX |
| chr7 | 27136145-27136425 | HOXA1 |
| chr17 | 46655791-46655837 | HOXB3 |
| chr16 | 22825790-22825885 | HS3ST2 |
| chr19 | 49339644-49339777 | HSD17B14 |
| chr20 | 20348122-20348415 | INSM1 |
| chr5 | 1887051-1887143 | IRX4 |
| chr2 | 182321830-182321983 | ITGA4 |
| chr2 | 182322268-182322409 | ITGA4 |
| chr2 | 182322891-182322981 | ITGA4 |
| chr17 | 73750051-73750237 | ITGB4 |
| chr17 | 73749594-73749691 | ITGB4 |
| chr1 | 111217635-111217816 | KCNA3 |
| chr1 | 215255702-215255769 | KCNK2 |
| chr6 | 62995727-62995877 | KHDRBS2 |
| chr22 | 50987205-50987270 | KLHDC7B |
| chr1 | 65991493-65991631 | LEPR |
| chr19 | 3786252-3786371 | MATK |

TABLE 3-continued

Cholangiocarcinoma DMRs using normal pancreas as controls

| Chromosome | Chromosome Coordinates | Gene Annotation |
|---|---|---|
| chr19 | 3785828-3786024 | MATK |
| chr1 | 156405616-156405739 | MAX.chr1.156405616-156405739 |
| chr10 | 23462417-23462527 | MAX.chr10.23462417-23462527 |
| chr11 | 14926602-14927148 | MAX.chr11.14926602-14927148 |
| chr14 | 61104539-61104618 | MAX.chr14.61104539-61104618 |
| chr18 | 13137148-13137759 | MAX.chr18.13137148-13137759 |
| chr18 | 53447550-53447661 | MAX.chr18.53447550-53447661 |
| chr2 | 66809242-66809304 | MAX.chr2. 66809242-66809304 |
| chr2 | 71116036-71116353 | MAX.chr2.71116036-71116353 |
| chr22 | 17850421-17850568 | MAX.chr22.17850421-17850568 |
| chr4 | 62067637-62067732 | MAX.chr4. 62067637-62067732 |
| chr6 | 10381594-10381699 | MAX.chr6.10381594-10381699 |
| chr6 | 1378408-1378478 | MAX.chr6.1378408-1378478 |
| chr7 | 25896389-25896501 | MAX.chr7.25896389-25896501 |
| chr7 | 27209650-27209687 | MIR196B |
| chr7 | 156798436-156798546 | MNX1 |
| chr4 | 174450408-174450497 | NBLA00301 |
| chr12 | 5541234-5541336 | NTF3 |
| chr12 | 5542167-5542272 | NTF3 |
| chr15 | 88800287-88800568 | NTRK3 |
| chr15 | 88801004-88801109 | NTRK3 |
| chr21 | 34395395-34395485 | OLIG2 |
| chr12 | 94543138-94543232 | PLXNC1 |
| chr19 | 46996516-46996841 | PNMAL2 |
| chr19 | 46997148-46997243 | PNMAL2 |
| chr16 | 23847825-23848025 | PRKCB |
| chr16 | 23847575-23847699 | PRKCB |
| chr7 | 157476955-157477032 | PTPRN2 |
| chr17 | 77179605-77180064 | RBFOX3 |
| chr5 | 80690040-80690227 | RNU5E |
| chr1 | 237205369-237205464 | RYR2 |
| chr16 | 51190008-51190146 | SALL1 |
| chr19 | 6753409-6753639 | SH2D3A |
| chr4 | 42399256-42399431 | SHISA3 |
| chr1 | 234261126-234261264 | SLC35F3 |
| chr10 | 106400259-106400346 | SORCS3 |
| chr2 | 5836452-5836524 | SOX11 |
| chr1 | 248020625-248020730 | TRIM58 |
| chr7 | 19157563-19157634 | TWIST1 |
| chr19 | 30018154-30018190 | VSTM2B |
| chr19 | 30016283-30016383 | VSTM2B |
| chr19 | 30017506-30017595 | VSTM2B |
| chr22 | 46367988-46368087 | WNT7B |
| chr8 | 56015654-56015761 | XKR4 |
| chr2 | 145273657-145273737 | ZEB2 |

Example II

This example describes the identification of markers for the detection of extra-hepatic CCA (eCCA).

Methods: Reduced-representation bisulfite sequencing (RRBS) was performed on DNA extracted from 18 frozen eCCA tissue samples and matched, adjacent benign biliary epithelia or liver parenchyma. Differentially methylated regions (DMRs) with at least 3 CpGs were ranked by area under the receiver operating characteristics curve (AUC) & by tumor:normal ratio and then technically validated by methylation specific PCR (MSP) on DNA from same samples. Best DMRs were selected for biological validation on DNA from independent tissues comprising 15 eCCA cases and 60 controls (6 adjacent bile duct, 18 adjacent liver, 18 white blood cell samples, 18 normal colon epithelia) using MSP. Biologically valid DMRs were then blindly assayed on DNA extracted from independent archival biliary brushing specimens including 14 perihilar (pCCA) & 4 distal (dCCA) cases and 18 matched cytology-negative controls (CTRL), 4 of which had primary sclerosing cholangitis (CTRL-PSC).

Results: From 5.5 million CpGs, 3674 significant DMRs were mapped; 43 were selected for technical validation (see, Table 4) from which 16 DMRs had an AUC of 0.75-1.0 (see, Table 5). In biological validation, 8 of these showed an AUC>0.75 in eCCA tissues. In brushings, methylated EMX1, HOXA1, VSTM2B.764, KCNA1, BMP3, SALL1, PTGDR, and RYR2, showed sensitivities of 100% 89%, 83%, 78%, 72%, 72%, 72%, and 72%, respectively, at 90% specificity. Primer information for the EMX1, HOXA1, VSTM2B.764, KCNA1, BMP3, SALL1, PTGDR, and RYR2 is provided in Table 6.

Conclusion: Whole-methylome discovery by next-generation DNA sequencing yielded novel, highly-discriminant methylation markers for eCCA. Results were validated in independent tissues as well as cytology brushings.

TABLE 4

45 DMRs selected for technical validation following reduced-representation bisulfite sequencing (RRBS) performed on DNA extracted from 16 frozen eCCA tissue samples.

| Gene Annotation | Chromosome and Chromosome Coordinates |
|---|---|
| ADAMTS10-RS | chr19:8675582-8675712 |
| ADAMTS17-FS | chr15:100881962-100882034 |
| BACH2-FS | chr6:91004976-91005235 |
| BNIP3-FS | chr10:133795886-133795981 |
| C12orf39-FS | chr12:21680721-21680828 |
| CUX2-FS | chr12:111471915-111472063 |
| DKFZP434H168-FS | chr16:56228418-56228445 |
| DOCK10.1367.1368-RS | chr2:225906664-225906766 |
| EDARADD-FS.fit | chr1:236559049-236559149 |
| ELM01.293-RS.fit | chr7:37487755-37487812 |
| ELM01.295-RS | chr7:37488645-37488836 |
| FADS2-RS | chr11:61596137-61596264 |
| FER1L4.300-FS | chr20:34189085-34189184 |
| FER1L4.301-FS | chr20:34189488-34189580 |
| GALNT13 | chr2:154728168-154728187 |
| GNA01-RS | chr16:56225334-56225426 |
| GPR150-RS | chr5:94957015-94957061 |
| KCNA1-FS | chr12:5019401-5019483 |
| KLF12-RS | chr13:74707214-74707396 |
| LRRC10B-FS.fit | chr11:61276688-61277038 |
| MATK.210-RS | chr19:3786125-3786199 |
| MAX.chr2.71503632-71503860-RS | chr2:71503632-71503860 |
| MAX.chr20.40321476-40321852-RS | chr20:40321476-40321852 |
| MAX.chr5.127537200-127537275-FS | chr5:127537200-127537275 |
| MAX.chr7.35226233-35226276-FS | chr7:35226233-35226276 |
| MDFI-RS | chr6:41606384-41606401 |
| NGFR-FS | chr17:47573867-47574084 |
| NTF3-RS | chr12:5542167-5542211 |
| NTRK3.634-RS | chr15:88800510-88800558 |
| PACSIN3-FS | chr11:47208766-47208861 |
| PTGDR-RS | chr14:52735457-52735485 |
| RYR2-RS | chr1:237206501-237206519 |
| S1PR1-FS | chr1:101702698-101702745 |
| SALL1-FS | chr16:51189969-51190019 |
| SEPTIN9.1286-FS | chr17:75370018-75370102 |
| ZFP3O-FS | chr19:38145754-38146121 |
| ZNF682-FS | chr19:20149796-20149923 |
| MAX.chr1.2574556-2574652-FS | chr1:2574556-2574652 |
| MAX.chr11.14926627-14926641-RS | chr11:14926627-14926641 |
| MAX.chr2.114260890-114260992-FS | chr2:114260890-114260992 |
| MAX.chr7.1705970-1706018-RS | chr7:1705970-1706018 |
| MAX.chr9.139085468-139085520-FS | chr9:139085468-139085520 |
| VSTM2B.764-RS | chr19:30019542-30019613 |

TABLE 5

Top 16 DMRs having an AUC > 0.75 from 45 DMRs selected for technical validation following reduced-representation bisulfite sequencing (RRBS) performed on DNA extracted from 16 frozen eCCA tissue samples.

| Gene Annotation | Chromosome and Chromosome Coordinates |
|---|---|
| BNIP3-FS | chr10:133795886-133795981 |
| DKFZP434H168-FS | chr16:56228418-56228445 |
| FER1L4.301-FS | chr20:34189488-34189580 |
| KCNA1-FS | chr12:5019401-5019483 |
| KLF12-RS | chr13:74707214-74707396 |
| MAX.chr2.71503632-71503860-RS | chr2:71503632-71503860 |
| MDFI-RS | chr6:41606384-41606401 |
| NTF3-RS | chr12:5542167-5542211 |
| PACSIN3-FS | chr11:47208766-47208861 |
| PTGDR-RS | chr14:52735457-52735485 |
| RYR2-RS | chr1:237206501-237206519 |
| S1PR1-FS | chr1:101702698-101702745 |
| SALL1-FS | chr16:51189969-51190019 |
| ZNF682-FS | chr19:20149796-20149923 |
| MAX.chr2.114260890-114260992-FS | chr2:114260890-114260992 |
| VSTM2B.764-RS | chr19:30019542-30019613 |

TABLE 6

Primer information for EMX1, HOXA1, VSTM2B.764, KCNA1, BMP3, SALL1, PTGDR, and RYR2, which showed sensitivities of 100% 89%, 83%, 78%, 72%, 72%, 72%, and 72%, respectively, at 90% specificity.

| Gene Annotation | AUC | Tissue Derivation | Forward Primer (5'-3') | Reverse Primer (5'-3') |
|---|---|---|---|---|
| EMX1 | 100% | iCCA derived | CGG GTT TTA GCG ATG TTT ATT TTA GTT TCG T (SEQ ID NO: 3) | CCT TTT CGT TCG TAT AAA ATT TCG TT (SEQ ID NO: 4) |

TABLE 6-continued

Primer information for EMX1, HOXA1, VSTM2B.764, KCNA1, BMP3, SALL1, PTGDR, and RYR2, which showed sensitivities of 100% 89%, 83%, 78%, 72%, 72%, 72%, and 72%, respectively, at 90% specificity.

| Gene Annotation | AUC | Tissue Derivation | Forward Primer (5'-3') | Reverse Primer (5'-3') |
|---|---|---|---|---|
| HOXA1 | 89% | iCCA derived | TGG GTT ATC GGT TTT TTA AGT TCG G (SEQ ID NO: 5) | GAA TTC CTC CCA ACC AAC CCT CTA CG (SEQ ID NO: 6) |
| VSTM2B.764 | 83% | eCCA derived | GTTTTAT AGGTTA GCGTCG AGTCGA (SEQ ID NO: 21) | ATCTATCGCC GATTACAAAA TCGAA (SEQ ID NO: 22) |
| KCNA1 | 78% | eCCA derived | GGGGGT AGGGAA GGAATA TTTTCGT C (SEQ ID NO: 23) | GACGCCCCT CTCAATTAAA CAATCG (SEQ ID NO: 24) |
| BMP3 | 72% |  | GTTTAAT TTTCGGT TTCGTC GTC (SEQ ID NO: 25) | CGCTACGAA ACACTCCGA (SEQ ID NO: 26) |
| SALL1 | 72% | eCCA derived | TTTCGTC GTTCGTT ATTAAG | ATCACGACG CTACACCCG AC |
|  |  |  | GGTTATT TTTAGAC (SEQ ID NO: 27) |  |
| PTGDR | 72% | eCCA derived | TTAGTAG TAAATTT TTTTGGT TTAGGG CGT (SEQ ID NO: 29) | AAAACTATCC GACCGCGAA TACGAA (SEQ ID NO: 30) |
| RYR2 | 72% | eCCA derived | TTGTAAG CGGTTA TAGTATT ATTACG G (SEQ ID NO: 31) | TAATCCCCGC GATTCCCGAA (SEQ ID NO: 32) |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method for measuring the methylation level of one or more CpG sites, the method comprising:
   a) extracting genomic DNA from a biological sample of a human individual suspected of having or having a neoplasm, wherein the neoplasm is intra-hepatic cholangiocarcinoma or extra-hepatic cholangiocarcinoma;
   b) treating the extracted genomic DNA with bisulfite;
   c) amplifying the bisulfite-treated genomic DNA with primers specific for EMX1, and at least one of ZNF781, HOXA1, and CYP26C1; and
   d) measuring the methylation level of the one or more CpG sites in the EMX1 and the at least one of ZNF781, HOXA1, and CYP26C1 by methylation-specific PCR, quantitative methylation-specific PCR, methylation sensitive DNA restriction enzyme analysis or bisulfite genomic sequencing PCR.

2. The method of claim 1, wherein the sample is a stool sample, a tissue sample, an intrahepatic tissue sample, an extrahepatic tissue sample, a blood sample, or a urine sample.

* * * * *